United States Patent
Soltz et al.

(10) Patent No.: US 7,148,073 B1
(45) Date of Patent: Dec. 12, 2006

(54) METHODS AND SYSTEMS FOR PREPARING A COPPER CONTAINING SUBSTRATE FOR ANALYSIS

(75) Inventors: David Soltz, San Jose, CA (US); Mehran Nasser-Ghodsi, Hamilton, MA (US); Harold Winters, San Jose, CA (US); John W. Coburn, San Jose, CA (US); Alexander Gubbens, Redwood City, CA (US); Gabor Toth, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 42 days.

(21) Appl. No.: 11/082,039

(22) Filed: Mar. 15, 2005

(51) Int. Cl.
*H01L 21/302* (2006.01)

(52) U.S. Cl. ............... 438/4; 438/8; 438/16; 438/708; 438/711; 438/720; 216/66; 216/78

(58) Field of Classification Search .............. 438/4, 438/8, 16, 708, 711, 714, 720; 216/65, 66, 216/78
See application file for complete search history.

(56) References Cited

U.S. PATENT DOCUMENTS

| | | |
|---|---|---|
| 4,559,450 A | 12/1985 | Robinson et al. |
| 4,842,683 A | 6/1989 | Cheng et al. |
| 5,215,619 A | 6/1993 | Cheng et al. |
| 5,614,060 A | 3/1997 | Hanawa |
| 5,740,226 A | 4/1998 | Komiya et al. |
| 5,770,099 A | 6/1998 | Rice et al. |
| 5,849,136 A | 12/1998 | Mintz et al. |
| 5,882,165 A | 3/1999 | Maydan et al. |
| 5,910,011 A | 6/1999 | Cruse |
| 5,926,690 A | 7/1999 | Toprac et al. |
| 5,976,310 A | 11/1999 | Levy |
| 6,040,198 A | 3/2000 | Komiya et al. |
| 6,072,147 A | 6/2000 | Koshiishi et al. |
| 6,072,178 A | 6/2000 | Mizuno |
| 6,074,518 A | 6/2000 | Imafuku et al. |
| 6,083,363 A | 7/2000 | Ashtiani et al. |
| 6,084,679 A | 7/2000 | Steffan et al. |
| 6,089,181 A | 7/2000 | Suemasa et al. |
| 6,110,287 A | 8/2000 | Arai et al. |
| 6,514,866 B1 * | 2/2003 | Russell et al. ............. 438/712 |
| 6,633,831 B1 | 10/2003 | Nikoonahad et al. |
| 6,730,237 B1 * | 5/2004 | Sievers et al. ............... 216/62 |
| 6,787,783 B1 * | 9/2004 | Marchman et al. ...... 250/492.2 |

(Continued)

FOREIGN PATENT DOCUMENTS

JP 08-222175 * 8/1996

(Continued)

*Primary Examiner*—George A. Goudreau
(74) *Attorney, Agent, or Firm*—Ann Marie Mewherter; Daffer McDaniel, LLP

(57) ABSTRACT

Methods and systems for preparing a substrate for analysis are provided. One method includes removing a portion of a copper structure on the substrate using an etch chemistry in combination with an electron beam. The etch chemistry is substantially inert with respect to the copper structure except in the presence of the electron beam. Other methods involve forming masking layers on a substrate that will protect the substrate during etching. For example, one method includes exposing a first portion of the substrate to an electron beam. A second portion of the substrate not exposed to the electron beam includes a copper structure. The method also includes exposing the substrate to a fluorine containing chemical. The fluorine containing chemical bonds to the first portion but not the second portion to form a fluorine containing layer on the first portion.

29 Claims, 9 Drawing Sheets

U.S. PATENT DOCUMENTS 6,843,927 B1 * 1/2005 Naser-Ghodsi .............. 216/84
6,921,722 B1 * 7/2005 Ogure et al. ................ 438/708
6,943,350 B1 * 9/2005 Nasser-Ghodsi et al. ... 250/310

FOREIGN PATENT DOCUMENTS

JP        2001-319923    * 11/2001

* cited by examiner

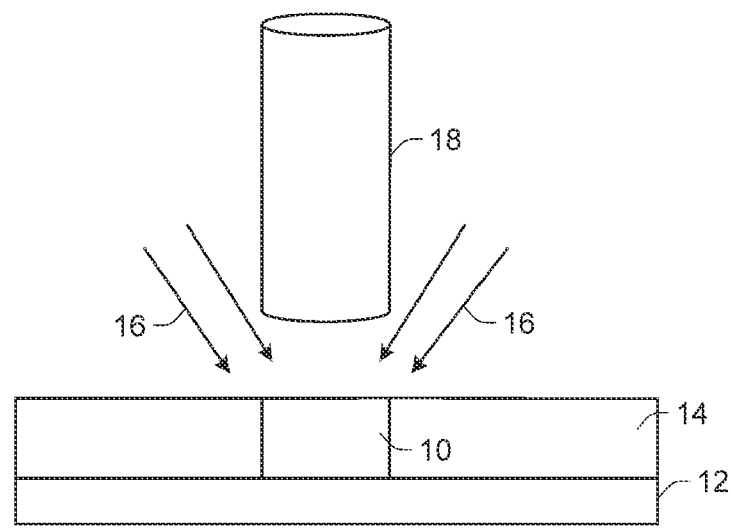
FIG. 1
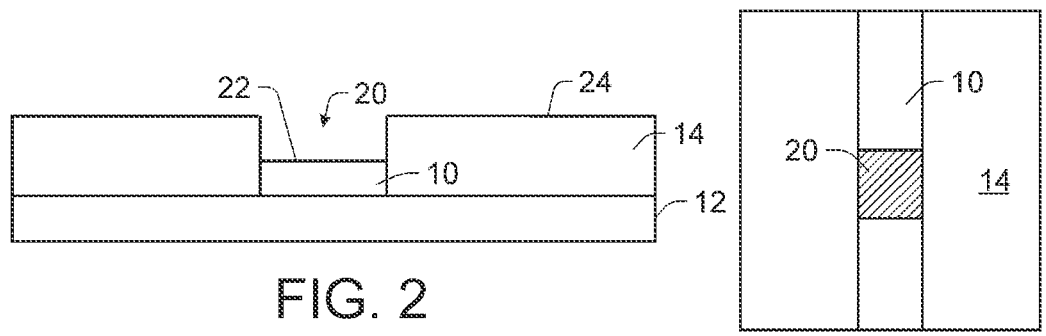 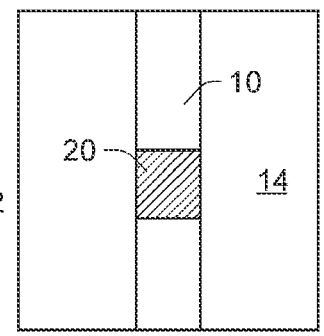
FIG. 2
FIG. 3
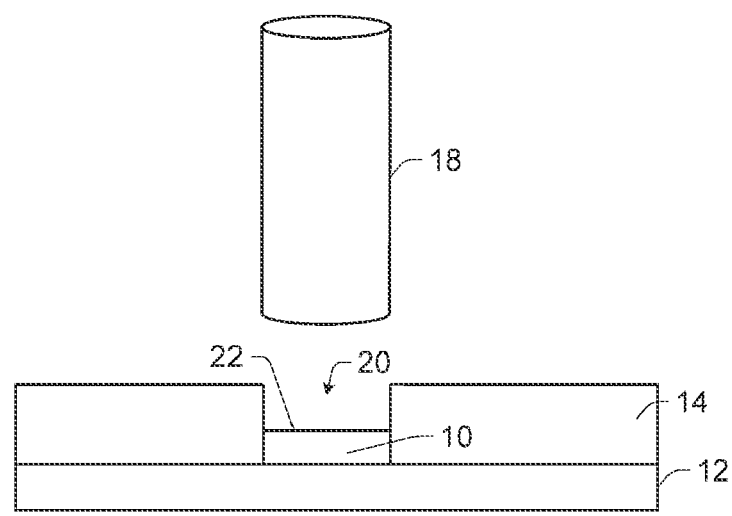
FIG. 4

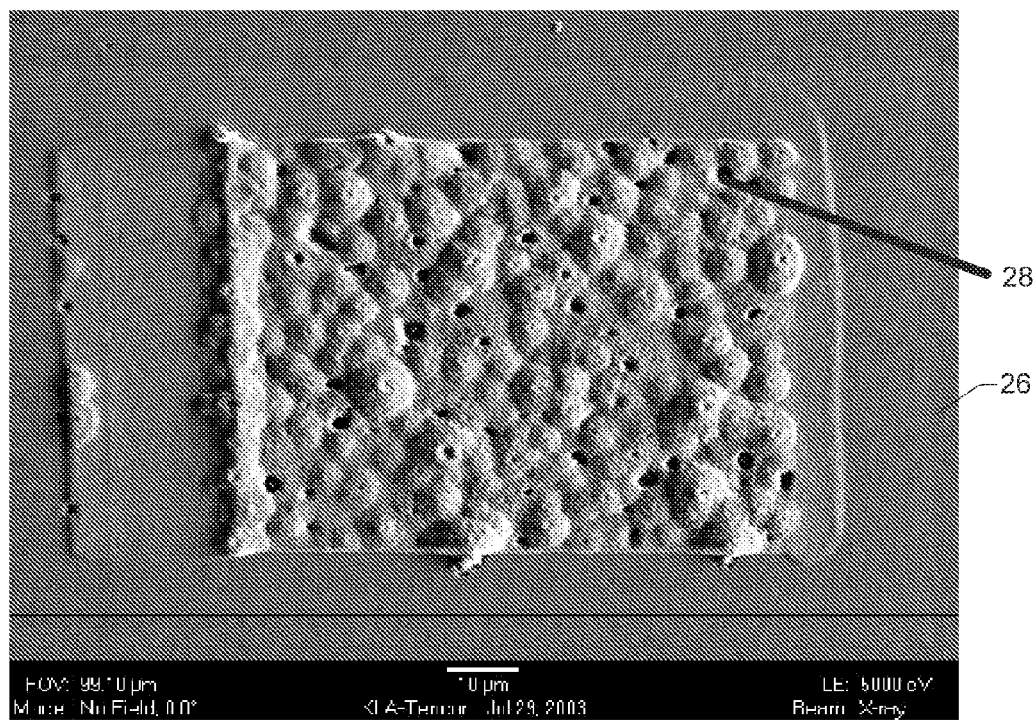
FIG. 5
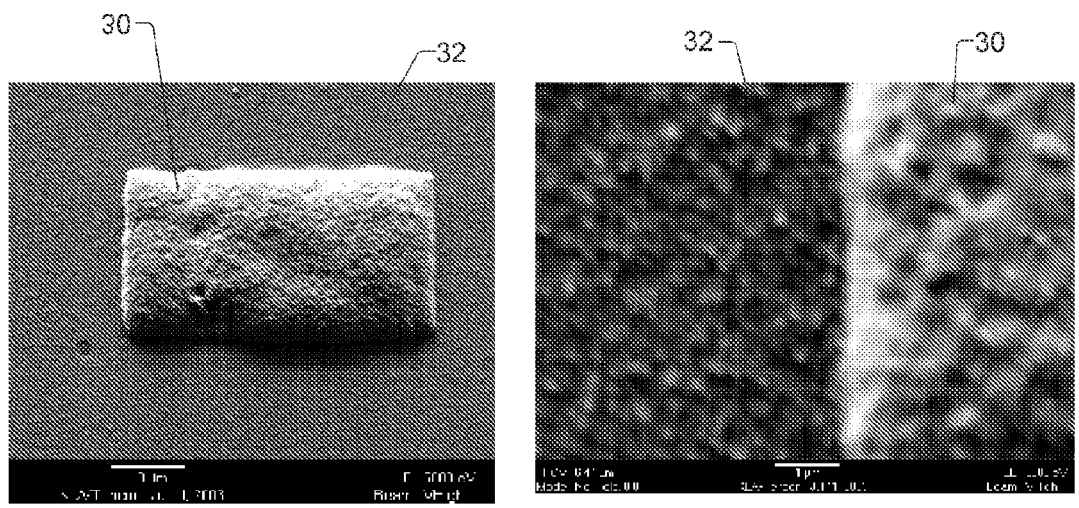
FIG. 6
FIG. 7

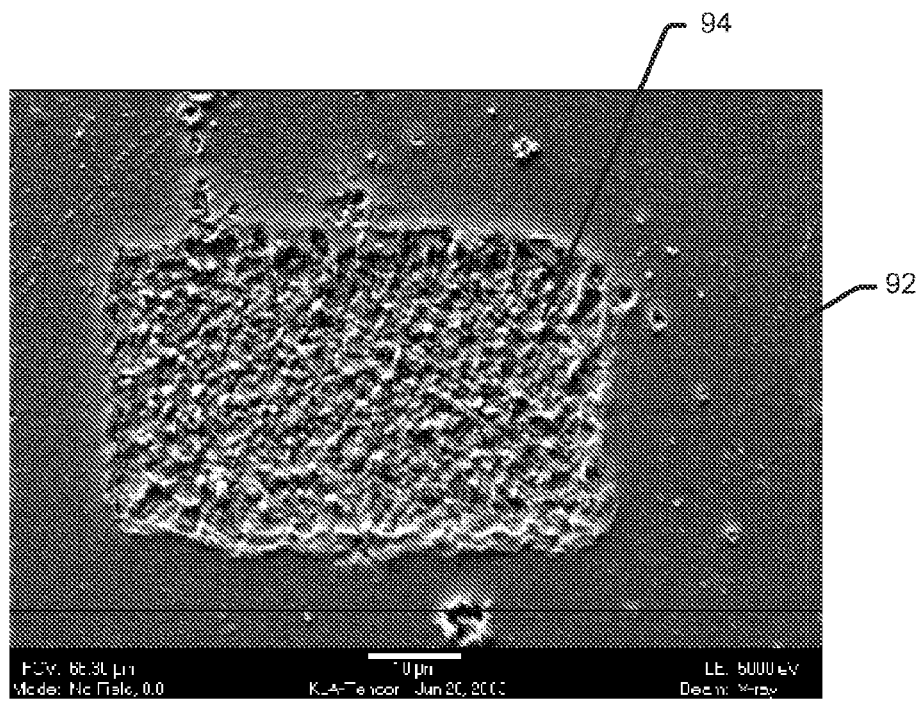
FIG. 12
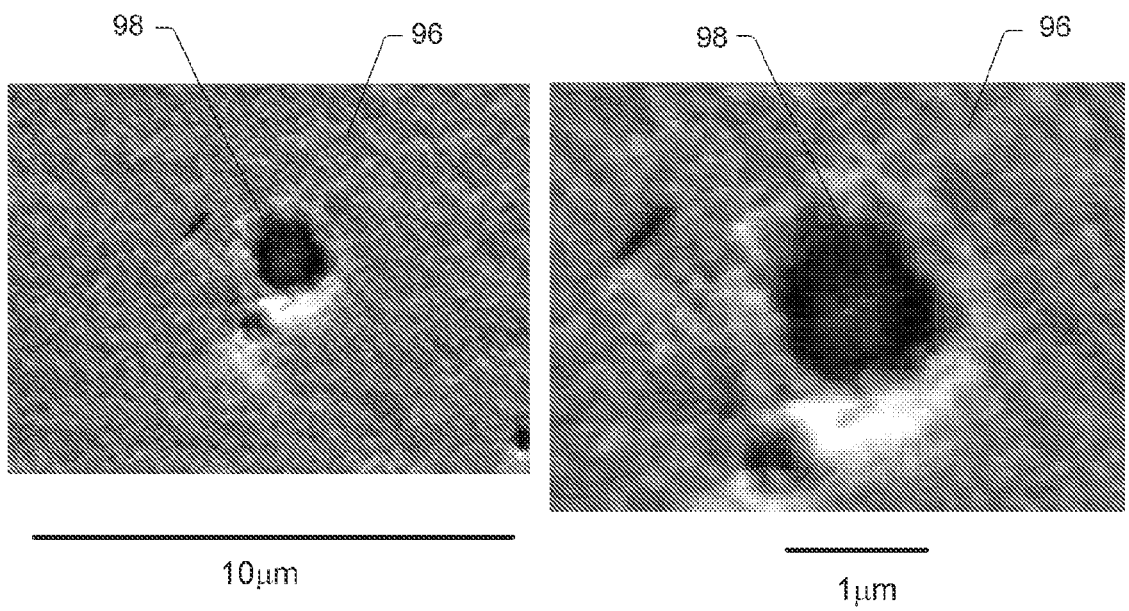
FIG. 13
FIG. 14

METHODS AND SYSTEMS FOR PREPARING A COPPER CONTAINING SUBSTRATE FOR ANALYSIS

BACKGROUND OF THE INVENTION

1. Field of the Invention

The present invention generally relates to methods and systems for preparing a copper containing substrate for analysis. Certain embodiments relate to methods and systems for removing a portion of a copper structure on a substrate using an etch chemistry in combination with an electron beam.

2. Description of the Related Art

The following description and examples are not admitted to be prior art by virtue of their inclusion in this section.

Fabricating semiconductor devices such as logic and memory devices typically includes processing a substrate such as a semiconductor wafer using a number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

As the dimensions of advanced semiconductor devices continue to shrink, the presence of defects in the semiconductor devices increasingly limits the successful fabrication, or yield, of the semiconductor devices. For example, incompletely filled vias formed on a wafer during deposition may cause an open circuit in, or complete failure of, one or more semiconductor devices formed in subsequent processing. Accordingly, defect detection, or "inspection," of semiconductor wafers is and will continue to be of significant importance in semiconductor development and manufacturing. In addition, review and analysis of defects is of significant importance in determining the cause of defects such that they may be corrected.

The ability to remove device film layers ("de-layer") or structures at select locations on a wafer in a localized and controllable fashion is critical for defect review and analysis during the device fabrication process. For example, removing a device film layer may allow a better view of a defect, particularly a subsurface or partially subsurface defect. In addition, removing a device film layer may enable analysis of the defect composition to be performed with less interference from the surrounding film layer.

Current techniques for de-layering of a substrate utilize ion beam etching, laser ablative etching, or mechanical abrasion using a micro-tip. Focused ion beam etching utilizes gallium ions to stimulate etching. Laser ablative techniques utilize lasers to heat the surface of the substrate to cause chemical and thermal reactions that remove the films. The mechanical abrasion technique uses micro-tips to remove the films around the defect.

Of the current techniques, ion beam etching is the most mature technique used to de-layer devices. However, when using an ion beam to stimulate etching, gallium ions from a source are implanted into the films, which can lead to changes in the optical, electrical, and mechanical properties of the etched features and the surrounding areas. The presence of gallium ions in the device can limit further processing of the device and the wafer in the fab, which would result in scrapping the entire wafer. In addition, during focused ion beam etching, the etched material may be deposited in the surrounding areas on the wafer. The other techniques currently used for de-layering of a substrate also have several disadvantages. For example, the laser ablative technique has low etch selectivity. In addition, the mechanical abrasion method has limited applications to certain large defects and films.

Accordingly, it would be advantageous to develop methods and systems for preparing a substrate for analysis by removing a portion of a structure or de-layering a structure on the substrate, which do not destroy or contaminate the substrate or the structure. In particular, it would be advantageous to develop methods and systems that can be used to remove a portion of a copper structure on a substrate such that the copper structure or defect thereof can be analyzed.

SUMMARY OF THE INVENTION

An embodiment of the invention relates to a method for preparing a substrate for analysis. The method includes removing a portion of a copper structure on the substrate using an etch chemistry in combination with an electron beam. The etch chemistry is substantially inert with respect to the copper structure except in the presence of the electron beam.

In one embodiment, the etch chemistry may include a chlorine-based chemistry. In some embodiments, the portion of the copper structure may have an area that is equal to or less than about 10 μm by about 10 μm. In another embodiment, the portion of the copper structure may have an area that is approximately equal to an area of the electron beam on the copper structure. The substrate may include a patterned wafer.

The method may also include illuminating the portion of the copper structure with light that is absorbed by a byproduct of the removing step. In one such embodiment, the light may be substantially coaxial with the electron beam. In another embodiment, the light and the electron beam may be directed to the portion of the copper structure at the same time.

In other embodiments, the method may include removing from the substrate a byproduct of the removing step using one or more chemicals. In one embodiment, the one or more chemicals may include an oxygen containing compound. In a different embodiment, the one or more chemicals may include xenon difluoride. In further embodiments, the one or more chemicals may include tetraethyl phosphine.

In a further embodiment, the method may include performing the analysis. The analysis may include inspection of the copper structure using the light. In another embodiment, the analysis includes inspection of the copper structure using the light and determination of a characteristic of a defect detected by the inspection.

In another such embodiment, the analysis may include inspection of the copper structure using the electron beam. In a different embodiment, the analysis may include inspection of the copper structure using the electron beam and determination of a characteristic of a defect detected by the inspection using the electron beam.

In some embodiments, the analysis may include inspection of the copper structure for subsurface or partially subsurface defects. In another embodiment, the analysis may include inspection of the copper structure and determination of a characteristic of a defect in the copper structure detected by the inspection. In a further embodiment, the analysis may include inspection of the copper structure for defects and root cause analysis of the defects. Each of the embodiments of the method described above may include any other step(s) described herein.

An additional embodiment relates to a system configured to prepare a substrate for analysis. The system includes a chemical delivery subsystem configured to deliver one or more chemicals to the substrate. The system also includes an electron delivery subsystem configured to deliver an electron beam to a portion of a copper structure on the substrate. The one or more chemicals in combination with the electron beam remove the portion of the copper structure on the substrate. The one or more chemicals are substantially inert with respect to the copper substrate except in the presence of the electron beam.

In one embodiment, the one or more chemicals include a chlorine-based chemistry. In another embodiment, the portion of the copper structure has an area that is equal to or less than about 10 µm by about 10 µm. In an additional embodiment, the portion of the copper structure has an area that is approximately equal to an area of the electron beam on the copper structure. In some embodiments, the substrate may include a patterned wafer.

In one embodiment, the system may include a light delivery subsystem that is configured to deliver light to the portion of the copper structure. The light is absorbed by a byproduct of the removal of the portion of the copper structure. In one such embodiment, the electron delivery subsystem and the light delivery subsystem may be configured to deliver the light and the electron beam substantially coaxially. In another embodiment, the electron delivery subsystem and the light delivery subsystem are configured to deliver the light and the electron beam to the portion of the copper at the same time. In some embodiments, the system may be configured to perform the analysis using the light delivery subsystem to inspect the copper structure. In a further embodiment, the system may be configured to perform the analysis using the light delivery subsystem to determine a characteristic of a defect in the copper structure.

In one embodiment, the chemical delivery subsystem may be configured to deliver one or more additional chemicals to the substrate. The one or more additional chemicals are selected to remove from the substrate a byproduct of the removal of the portion of the copper structure. In one such embodiment, the one or more additional chemicals include an oxygen containing compound. In a different embodiment, the one or more additional chemicals include xenon difluoride. In a further embodiment, the one or more additional chemicals include tetraethyl phosphine.

In another embodiment, the system may be configured to perform the analysis using the electron delivery subsystem to inspect the copper structure. In a further embodiment, the system may be configured to perform the analysis using the electron delivery subsystem to inspect the copper structure and to determine a characteristic of a defect detected by inspection.

In some embodiments, the system may be configured to perform the analysis, and the analysis may include inspection of the copper structure and determination of a characteristic of a defect detected by the inspection. In another embodiment, the system may be configured to perform the analysis, and the analysis may include inspection of the copper structure and root cause analysis of defects detected by the inspection. The system may be further configured as described herein.

Another embodiment relates to a different method for preparing a substrate for analysis. This method includes exposing a first portion of the substrate to an electron beam. A second portion of the substrate not exposed to the electron beam includes a copper structure. The method also includes exposing the substrate to a fluorine containing chemical. The fluorine containing chemical bonds to the first portion but not the second portion to form a fluorine containing layer on the first portion. In addition, the method includes exposing the substrate to an etch chemistry. The etch chemistry does not etch the first portion of the substrate due to the fluorine containing layer. The etch chemistry etches the copper structure in the second portion of the substrate.

In one embodiment, the etch chemistry includes a chlorine based etch chemistry. In another embodiment, the fluorine containing chemical includes carbon tetrafluoride. In some embodiments, the first portion of the substrate includes an additional copper structure. Additionally, or alternatively, the first portion of the substrate includes an additional portion of the copper structure. Each of the embodiments of the method described above may include any other step(s) described herein.

A further embodiment includes yet another different method for preparing a substrate for analysis. This embodiment includes exposing the substrate to a fluorine containing chemical. The fluorine containing chemical bonds to the substrate to form a fluorine containing layer on the substrate. The method also include removing copper in a first portion of the substrate by directing an electron beam to the first portion in the presence of an etch chemistry. Other portions of the substrate not exposed to the electron beam are not removed due to the fluorine containing layer.

In some embodiments, prior to the exposing step, the method may include cleaning the substrate to remove oxide present on the substrate. In another embodiment, prior to the exposing step, the method may include directing the electron beam to the substrate to prepare the substrate for bonding with the fluorine containing chemical. In a different embodiment, during the exposing step, the method may include directing the electron beam to the substrate. In this embodiment, the fluorine containing chemical may be substantially inert with respect to the substrate except in the presence of the electron beam. The etch chemistry may include a chlorine-based chemistry. Each of the embodiments of the method described above may include any other step(s) described herein.

Yet another embodiment relates to another method for preparing a substrate for analysis. This method includes removing a portion of a copper structure on the substrate using an etch chemistry in combination with an electron beam. The etch chemistry is substantially inert with respect to the copper structure except in the presence of the electron beam. The method also includes inhibiting removal of other portions of the copper structure and other copper structures on the substrate during the removing step by exposing the substrate to a fluorine containing chemical during the removing step. The fluorine containing chemical bonds with the other portions of the copper structure and the other copper structures on the substrate.

In one embodiment, the etch chemistry includes a chlorine-based chemistry. In some embodiments, the fluorine containing chemical includes xenon difluoride. Each of the embodiments described above may include any other step(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIG. 1 is a schematic diagram illustrating a partial cross-sectional view of a copper structure on a substrate, which is exposed to an etch chemistry in combination with an electron beam;

FIG. 2 is a schematic diagram illustrating a partial cross-sectional view of the substrate of FIG. 1 in which a portion of the copper structure is removed;

FIG. 3 is a schematic diagram illustrating a partial top view of the substrate of FIG. 2;

FIG. 4 is a schematic diagram illustrating a partial cross-sectional view of the substrate of FIG. 2 and an electron beam configured to perform analysis of the copper structure;

FIGS. 5–7 are scanning electron microscope (SEM) images of copper layers formed on a substrate, of which a portion was removed using an etch chemistry in combination with an electron beam;

FIGS. 12–13 are SEM images of copper layers formed on a substrate, a portion of which was removed using an etch chemistry in combination with an electron beam and a light beam;

FIG. 14 is a higher magnification SEM image of the substrate shown in FIG. 13;

Figure 8:
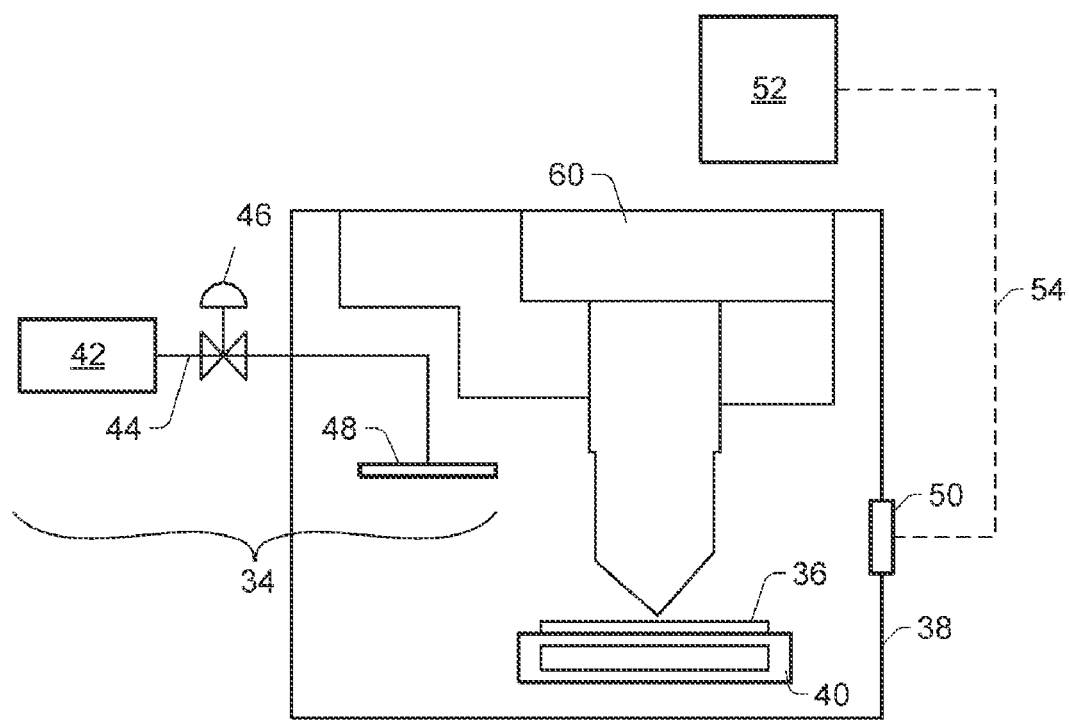
FIGS. 8–9 are schematic diagrams illustrating side views of different embodiments of a system configured to prepare a substrate for analysis.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "substrate" is generally defined as a wafer or a reticle. As used herein, the term "wafer" generally refers to a substrate formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate. Such a wafer is commonly referred to as a "virgin wafer." Alternatively, a wafer may include one or more layers formed upon a substrate. For example, such layers may include, but are not limited to, a resist, a dielectric material, and a conductive material. A resist or a "photoresist" may include any material that may be patterned by an optical lithography technique, an e-beam lithography technique, or an X-ray lithography technique. Examples of a dielectric material include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "integrated circuit." In addition, other devices such as microelectromechanical (MEMS) devices and the like may also be formed on a wafer.

A "reticle," or a "mask," is generally defined as a substantially transparent substrate having substantially opaque regions formed thereon and configured in a pattern. The substrate may include, for example, a glass material such as quartz. The substantially opaque regions may be formed of a material such as chromium. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source. Many different types of reticles are known in the art, and the term reticle as used herein is intended to encompass all types of reticles.

As used herein, the term "structure" generally refers to any structure formed on a substrate that has some lateral extent in three-dimensions (i.e., a width as well as a height).

Examples of structures include patterned structures formed on semiconductor wafers such as contact structures and interconnect structures. Patterned structures may be formed on semiconductor wafers using any process known in the art (e.g., a sequence of processes including lithography, etch, cleaning, deposition, chemical-mechanical polishing). Therefore, in one embodiment, the substrate may be a patterned wafer. In some such embodiments, the patterned wafer may be a product wafer. As such, the structure may be formed in a test area on the product wafer or in a device area on the product wafer. In other words, the structure may be a test structure or a device structure.

In addition, a structure may be a non-patterned layer formed on a substrate. The structure may be formed of any material known in the art such as a resist, a conductive material, and an insulating material. The embodiments described herein are particularly suitable for use with copper structures. Although embodiments are described herein with respect to copper, it is to be understood that the methods and systems described herein may be used to remove another material on a substrate such as a dielectric material or tungsten with appropriate changes to one or more parameters of the methods and/or systems described herein. For example, the methods and systems described herein can be used to remove other materials on a substrate by selecting an etch chemistry that is normally inert with respect to a material and activating the etch chemistry using an electron beam incident on the portion of the material to be removed.

Methods and systems are described herein that may be used for removing device film layers (de-layering) and structures at selective locations in a controllable fashion. Such de-layering is critical for defect review and analysis during the device fabrication process. As described further above, current techniques for de-layering include ion beam etching, laser ablative etching, and mechanical abrasion using a micro-tip. These techniques have disadvantages such as causing changes in the optical, electrical, and mechanical properties of the etched features and surrounding areas and contamination of the substrate, all of which can effectively destroy the substrate.

Electron beam assisted chemical etching as described further herein has many advantages over these techniques. For example, using an electron beam instead of an ion beam for etching eliminates the ion contamination and the collateral damage that the ion beam causes to surrounding areas. Therefore, the methods and systems described herein are compatible with front end of the line (FEOL) processing and back end of the line (BEOL) processing, and wafers that have been de-layered as described herein can be returned to the process line. In addition, another advantage of electron beam assisted chemical etching is the high degree of etch selectivity and endpoint detection. Furthermore, since the methods and systems described herein have a relatively high throughput, the time in which the root cause of defects can be correctly identified using these methods and systems may be significantly lower than currently used methods and systems.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIGS. 1–4 illustrate an embodiment of a method for preparing a substrate for analysis. As shown in FIG. 1, copper structure 10 is formed on substrate 12. Substrate 12 may include any of the substrates described above. In this example, copper structure 10 is an interconnect structure formed in material 14. Material 14 may include any insulating material known in the art. Although only one copper structure is shown on substrate 12 in FIGS. 1–4, it is to be understood that two or more copper structures may be formed on the substrates described herein. The copper structures may be similarly configured (e.g., all of the copper structure may be interconnects). Alternatively, the copper structures may be differently configured. For example, interconnect structures as well as contact structures may be formed in material 14. In another example, the copper structure may be a defect that is at least partially formed of copper. In a different example, the copper structure may be a non-patterned layer of copper formed on material 14 or substrate 12. In any case, copper structure 10 may be formed on the substrate using any process(es) known in the art (such as etching, followed by deposition and chemical-mechanical polishing).

The method includes removing a portion of the copper structure on the substrate using an etch chemistry in combination with an electron beam. For example, as shown in FIG. 1, a portion of copper structure 10 is exposed to etch chemistry 16 in combination with electron beam 18. In some embodiments, the etch chemistry may include a chlorine-based chemistry. Alternatively, the etch chemistry may include a different etch chemistry that is suitable for etching copper such as a bromine-based chemistry or even an iodine-based chemistry. These etch chemistries may include one or more chemicals. For example, a chlorine-based etch chemistry may include one or more chlorine containing chemicals possibly in combination with other chemicals.

The selection of an etch chemistry may vary depending on, for example, the composition of copper structure 10, the composition of material 14, and the composition of any other materials on the substrate that might be exposed to the etch chemistry. For example, the etch chemistry may be selected such that it does not substantially etch materials on the substrate other than copper structure 10. In this manner, the etch chemistry may not damage the substrate or other materials or features exposed to the etch chemistry.

The etch chemistry is also preferably substantially inert with respect to the copper structure except in the presence of the electron beam. In other words, the methods described herein use etch chemistries that are either nominally inert or less reactive than standard etch chemistries that are used to etch copper. Examples of such etch chemistries may include one or more chemicals such as chlorine gas ($Cl_2$), Phosgene ($COCl_2$), hydrogen chloride (HCl), and hydrogen bromide (HBr). Further examples of one or more chemicals that can be used in the methods and systems described herein include, but are not limited to, bromine gas ($Br_2$), iodine gas ($I_2$), tetrachloroethene ($C_2Cl_4$), and pentachloroethane ($CHCl_2CCl_3$), in combination with ethanol (EtOH) and/or methanol (MeOH).

In this manner, the etch chemistry can be used in combination with the electron beam to etch only those portions of a copper structure that are exposed to the electron beam. Selecting such an etch chemistry will reduce, and may even prevent, removal of other portions of the copper structure or other copper structures on the substrate. In this manner, the methods and systems described herein may be used for truly localized etching even though a much larger portion of the substrate (and perhaps the entire substrate) is exposed to the etch chemistry. As such, even if a large number of copper structures are present on the substrate, a portion of individual copper structures (e.g., one or more) may be removed separately and independently. The etch chemistry may be selected such that the etch chemistry does not form or deposit unwanted byproducts on the surface of the substrate such as carbon containing byproducts. In addition, the one or more chemicals included in the etch chemistry may be selected to include those chemicals (e.g., $Cl_2$, HCl, and HBr), which will form relatively volatile etch byproducts.

Since the portion of the copper structure that is removed will be largely limited to the area which is illuminated by the electron beam, the area of the removed portion of the copper structure may be relatively small. In other words, the area of the portion of the material that is removed may vary depending on, for example, the area on the substrate that is illuminated by the electron beam. For example, in the methods and systems described herein, etching takes place only in the presence of etchant gases in combination with the electron beam. Therefore, the portion of the copper structure may have an area that is approximately equal to an area of the electron beam on the copper structure. In addition, the area of the electron beam, and thereby the area of the removed material, may be altered depending on, for example, the lateral dimensions of the structure, the area that is selected for removal, the analysis that is to be carried out on the structure, the characteristics of the material being removed, and/or the characteristics of the substrate.

In one particular example, the area of the material that is removed is preferably kept at a minimum (to avoid damaging or destroying neighboring structures if present) while allowing enough of the structure to be removed such that analysis can be successfully completed. In one embodiment, the portion of the copper structure that is removed has an area that is equal to or less than about 10 µm by about 10 µm. Therefore, the area on the substrate in which material is removed is relatively small, particularly when compared to the amount of material that is typically removed by other de-layering processes. In this manner, the methods and systems described herein may be used for high resolution, localized etching of copper structures.

The controllability provided in the copper removal methods described herein imparts several advantages to the methods and systems described herein. For example, the methods and systems described herein may be used to remove copper in a relatively small area on the substrate, which will largely be defined by the cross-sectional area of the electron beam. In this manner, the methods and systems described herein are advantageous in that they can be used to examine individual copper structures on a patterned wafer without causing damage to other copper structures on the patterned wafer. As such, the systems and methods can be used to examine one or more individual copper structures on a product wafer without damaging the product wafer such that it is no longer suitable for fabrication. For example, the systems and methods described herein may be used to remove a portion of copper test structures on a product wafer without removing any portion of copper device structures on the wafer.

As shown in FIG. 2, etch chemistry 16 in combination with electron beam 18 removed portion 20 of copper structure 10. As further shown in FIG. 2, the remaining portion of the copper structure has upper surface 22 that is lower than upper surface 24 of material 14. Therefore, the entire thickness of the copper structure upon which the electron beam is incident is not removed. However, the depth to which the structure is removed may vary depending on, for example, the analysis that is to be performed on the structure. For example, the entire thickness of the portion of the copper structure upon which the electron beam is incident may be removed. The thickness of the portion of the copper structure that is removed may be varied, for example, by changing the time during which the copper structure is exposed to the electron beam since removal of the portion of the copper structure will be substantially reduced, and even eliminated, without the electron beam.

As shown in FIG. 3, portion 20 of copper structure 10 that is removed is located centrally within the copper structure and spans the width of the copper structure. However, it is to be noted that the portion that is removed may be located near or at one end of the copper structure, an "end" being defined as the shorter lateral boundaries of the copper structure. In addition, unlike the removed portion shown in FIGS. 1–4, the removed portion may be located entirely within the copper structure (as opposed to abutting the lateral boundary of the material). Furthermore, the position of the removed portion within the copper structure may vary depending on, for example, the location of other structures on the substrate or to be formed on the substrate (e.g., device structures or other structures that will be formed above or below the copper structure).

The method may also include analyzing copper structure 10. For example, the copper structure may be inspected to determine if defects are present in the copper structure. In another example, the analysis may include inspection of the copper structure for subsurface or partially subsurface defects. In one embodiment, analyzing the copper structure may be performed using an electron beam. In one particular embodiment, as shown in FIG. 4, electron beam 18 that was used to remove portion 20 of copper structure 10 may also be used to inspect the copper structure. In another embodiment, the analysis may include determination of a characteristic of a defect detected by the inspection using the electron beam.

Parameters of the electron beam used to remove the portion of the copper structure may be different than those that are used to analyze the structure. In particular, if the same electron beam is used to remove the portion of the structure and to analyze the structure, the parameters of the subsystem used to deliver the electron beam (which may be configured as described herein) may be changed between removal and analysis to change one or more characteristics of the electron beam (e.g., energy, focus, etc.). The parameters of the electron beam may vary depending upon, for example, the size of the structure, the composition of the structure, the composition of the substrate, or the composition of the layer of the substrate upon which the feature is formed. Selection of appropriate parameters for analysis will be obvious to one of ordinary skill the art.

When analyzing the remaining portion of the structure with the same electron beam that is used for removal, the substrate may be tilted relative to the electron beam after the portion of the structure is removed and before the structure is analyzed. In this manner, the electron beam may be arranged at an appropriate viewing angle with respect to the remaining portion of the structure. The substrate may be tilted by altering the position of a stage (not shown) upon which the substrate is disposed. Alternatively, or in addition, the electron beam may be tilted relative to the substrate after the portion of the structure is removed and before analysis such that the electron beam is at an appropriate viewing angle during analysis. The electron beam may be tilted by altering one or more parameters of an electron delivery subsystem that is configured to deliver the electron beam to the substrate.

In addition, parameters of the removal process may be changed during analysis of the structure. For example, if the analysis is to be performed after the removal is complete, the etch chemistry may be removed from the chamber in which the substrate is disposed such that further etching of the structure does not take place during analysis.

In one such embodiment, electron beam 18 may be used to image the copper structure using a technique such as scanning electron microscopy. The image of the copper structure may then be used for defect detection and/or review or to determine characteristics of the copper structure. For example, the information generated by imaging of the structure by the electron beam may be used to detect voids and other subsurface defects in the copper structure.

In another embodiment, electron beam 18 may be used to image the copper structure as the copper is being removed. In this manner, the structure and the de-layering process can be monitored and recorded, possibly in real time, which may provide further information about the copper structure and the de-layering process. In this manner, the analysis may be performed during the removal using the electron beam. The information generated by imaging of the structure by the electron beam may also be used to determine an endpoint of the process and/or to optimize the de-layering process. In addition, analysis of the structure using the electron beam may also be performed after removal as described above.

The analysis may also include inspection of the copper structure for defects and root cause analysis of the defects. For example, in another embodiment, the electron beam may be used to determine a composition of the copper structure using a technique such as energy dispersive x-ray spectroscopy (EDX or EDS) or Auger electron spectroscopy (AES). In this manner, defects such as foreign material may be detected in the copper structure. Generally, in the EDX technique, a beam of electrons is directed to a surface of the structure. The copper structure may emit secondary electrons and a characteristic x-ray in response to the directed beam of electrons. The characteristic x-ray may be detected by a semiconductor x-ray detector and may be subjected to energy analysis. The x-ray spectrum may be analyzed to determine a composition of the copper structure. Examples of EDX systems and methods are illustrated in U.S. Pat. No. 4,559,450 to Robinson et al., U.S. Pat. No. 6,072,178 to Mizuno, and U.S. Pat. No. 6,084,679 to Steffan et al., which are incorporated by reference as if fully set forth herein.

In a different embodiment, removing the portion of the structure may be performed using one electron beam, and analyzing the structure may be performed using a different electron beam. In such an embodiment, the different electron beams may be arranged at a predetermined tilt position with respect to the substrate. In this manner, after a substrate is placed on a stage coupled to the analysis electron beam, the position of the stage may not have to be altered before analysis can be performed. In such embodiments, the electron beams may be generated by different electron delivery subsystems coupled to different stages. In other words, the electron delivery subsystems (although may be included in one system such as a cluster tool) preferably are configured such that the environment in which removal is performed is separated from the environment in which analysis is performed to prevent further removal of the structure being analyzed.

In another embodiment, an x-ray analysis system (not shown) may be used to determine a characteristic of the copper structure. For example, a composition of a structure can be determined using a technique such as x-ray photoelectron spectroscopy (XPS or ESCA) or x-ray fluorescence spectrometry (XRF). In another example, an x-ray reflectance (XRR) technique may be used to measure a characteristic of a structure such as a concentration of an element in a structure. Examples of x-ray reflectance methods and systems are illustrated in U.S. Pat. No. 5,740,226 to Komiya et al., U.S. Pat. No. 6,040,198 to Komiya et al., and U.S. Pat. No. 6,633,831 to Nikoonahad et al., which are incorporated by reference as if fully set forth herein. The x-ray analysis system may be configured as described in these patents. In other embodiments, analysis of the structure may be performed using any other analytical technique known in the art.

FIGS. 5–7 illustrate scanning electron microscope (SEM) images of substrates that include copper structures processed as described herein. The copper structures on the substrates shown in FIGS. 5–7 are unpatterned copper layers. The substrate shown in FIG. 5 was exposed to an electron beam having the following parameters: current=5 nA, energy=5 kV, for 15 minutes in the presence of a residual chlorine gas ($Cl_2$) flow. The field of view (FOV) of the electron beam on copper layer 26 was about 80 µm. As shown in FIG. 5, area 28 of the copper layer that reacted with the chlorine gas is sharply defined by the electron beam exposure area. The area of the copper layer that was exposed to the electron beam reacted with the chlorine gas to form copper chloride (CuCl), which is not volatile but can be removed as described further herein.

The substrate shown in FIG. 6 was disposed in the chamber of an electron delivery subsystem. A burst of bromine ($Br_2$) gas was introduced into the chamber at a pressure of about 5e-4 Torr. The electron beam was turned off during introduction of the burst of gas, but was turned on immediately afterward as the chamber was pumped down to a pressure of 1e-5 Torr. The electron beam had the following parameters: current 1.6 nA, energy 2 kV. The area of the copper layer that was exposed to the electron beam reacted with the bromine gas to form copper bromide (CuBr), which is not volatile but can be removed as described further herein.

As with the substrate illustrated in FIG. 5, area 30 of copper layer 32 on the substrate shown in FIG. 6 that reacted with the bromine gas is limited substantially to the area that was exposed to the electron beam. The image shown in FIG. 7 is a partial image of the reacted area shown in FIG. 6 in which the zoom was adjusted to show the detail of the edge definition of the reacted area, which does not vary by more than about 100 nm across the edge of the reacted area. Therefore, the area of the copper layer that reacted with the bromine gas is sharply defined by the area of exposure by the electron beam.

The above described examples are merely intended to illustrate the capability of the methods and systems described herein and are not intended to be limiting examples of the present invention. In particular, the images shown in FIGS. 5–7 illustrate that the reactivity of the copper layer is substantially limited to the area of the copper layer that was exposed to the etch chemistry in the presence of the electron beam. Therefore, the methods and systems described herein can be used for truly localized removal of copper structures on a substrate. In addition, as shown in FIGS. 5–7, the portions of the copper layer that were not exposed to the electron beam have not reacted with the etch chemistry. As such, the portion of the copper layer that was not exposed to the electron beam can be used in the fabrication of semiconductor devices if the substrate is a product wafer. Furthermore, the substrates shown in FIGS. 5–7 illustrate that the copper layer can be reacted with different gases that are substantially inert with respect to copper except when "activated" by the electron beam. In other words, the electron beam will catalyze the reaction in the area defined by the electron beam.

FIG. 8 illustrates one embodiment of a system that is configured to prepare a substrate for analysis. In particular, the system shown in FIG. 8 can be used to perform one or more embodiments of the methods described herein. The system includes chemical delivery subsystem 34. Chemical delivery subsystem 34 is configured to deliver one or more chemicals (not shown) to substrate 36. In other words, the chemical delivery subsystem is configured to deliver one or more chemicals to process chamber 38 in which substrate 36 is disposed upon stage 40. The one or more chemicals may include any of the chemicals described above. For example, the one or more chemicals may include a chlorine-based chemistry, a bromine-based chemistry, an iodine-based chemistry, or any other etch chemistry known in the art.

Chemical delivery subsystem 34 may include gas source (s) 42, tubing 44 coupled to gas source(s) 42, valve 46 coupled to tubing 44, and dispenser 48. The one or more chemicals may flow from gas source(s) 42 through tubing 44 and valve 46 to dispenser 48. The dispenser allows the one or more chemicals to be released into process chamber 38, preferably in a controllable manner. The gas source(s), tubing, valve, and dispenser may include any such appropriate components known in the art. The chemical delivery subsystem may also include many other components known in the art. In addition, the chemical delivery subsystem may have any configuration known in the art. Additional examples of chemical delivery subsystems are illustrated in U.S. Pat. No. 4,842,683 to Cheng et al., U.S. Pat. No. 5,215,619 to Cheng et al., U.S. Pat. No. 5,614,060 to Hanawa, U.S. Pat. No. 5,770,099 to Rice et al., U.S. Pat. No. 5,882,165 to Maydan et al., U.S. Pat. No. 5,849,136 to Mintz et al., U.S. Pat. No. 5,910,011 to Cruse, U.S. Pat. No. 5,926,690 to Toprac et al., U.S. Pat. No. 5,976,310 to Levy, U.S. Pat. No. 6,072,147 to Koshiishi et al., U.S. Pat. No. 6,074,518 to Imafuku et al., U.S. Pat. No. 6,083,363 to Ashtiani et al., U.S. Pat. No. 6,089,181 to Suemasa et al., U.S. Pat. No. 6,110,287 to Arai et al., and U.S. Pat. No. 6,633,831 to Nikoonahad et al., which are incorporated by reference as if fully set forth herein.

Chemical delivery subsystem 34, process chamber 38 and stage 40 may be further configured as described in these patents. For example, process chamber 38 may include pressure gauge 50. Pressure gauge 50 may be configured to measure a pressure within the process chamber. The pressure gauge may be coupled to processor 52 by transmission medium 54. Transmission medium 54 may include any appropriate transmission medium known in the art. In addition, the transmission medium may include "wired" and "wireless" portions. Processor 52 may be configured to alter one or more parameters of the system depending on the pressure measured by pressure gauge. In a similar manner, processor 52 may be coupled to other components of the system (e.g., valve 46) and may be configured to alter a parameter of the valve or other parameters of the system depending on the process being carried out in chamber 38.

The system also includes electron delivery subsystem 60. Electron delivery subsystem 60 is configured to deliver an electron beam (not shown) to a portion of a copper structure (not shown) on substrate 36. The electron delivery subsystem may be further configured as described herein. The one or more chemicals delivered by chemical delivery subsystem 34 in combination with the electron beam delivered by electron delivery subsystem 60 removes the portion of the copper structure on the substrate. In particular, the one or more chemicals are substantially inert with respect to the copper structure except in the presence of the electron beam. In this manner, the system may be used for localized copper removal on a substrate. The portion of the copper structure may be configured as described above.

Byproducts of the reactions between the material(s) and the one or more chemicals may be desorbed from the substrate as described further herein. The system may include one or more pumps (not shown) that are coupled to the process chamber. The one or more pumps may be configured to remove such byproducts from the process chamber thereby reducing the possibility that the byproducts may be deposited onto other areas on the substrate. The pump(s) may be any appropriate pumps known in the art.

The system shown in FIG. 8 may also include an analysis subsystem, which is configured to perform analysis of the copper structure. The analysis subsystem may be configured to perform analysis as described herein. For example, the analysis may include inspecting the copper structure for subsurface or partially subsurface defects. The analysis subsystem may be configured to determine a characteristic of a defect detected by inspection, a composition of the structure, or any of the other characteristics described herein. In addition, the analysis may include inspection of the copper structure and root cause analysis of defects detected by the inspection.

In one embodiment, the electron delivery subsystem may be used as an analysis subsystem. For example, the system may be configured to perform the analysis using the electron delivery subsystem to inspect the copper structure. In addition, the system may be configured to perform the analysis using the electron delivery subsystem to determine a characteristic of a defect detected by inspection. Furthermore, electron delivery subsystem 60 may be configured to measure a characteristic of the structure using the electron beam.

Parameters of the electron beam used for removal may be different than parameters of the electron beam that are used for analysis. The parameters of the electron beam may be altered between removal and analysis by altering one or more parameters of the electron delivery subsystem. The parameter(s) of the electron delivery subsystem may be altered or controlled by processor 52 in some embodiments.

In a different embodiment, the analysis subsystem may include an x-ray analysis system (not shown) such as those described above or any of those known in the art. The analysis subsystem may be coupled to the system shown in FIG. 8 in any manner. For example, the analysis subsystem and the system shown in FIG. 8 may be disposed in one housing, coupled by a common processor, a common substrate handler, a common power source, a transmission medium, etc. The embodiment of the system shown in FIG. 8 may be further configured as described herein.

Figure 9:
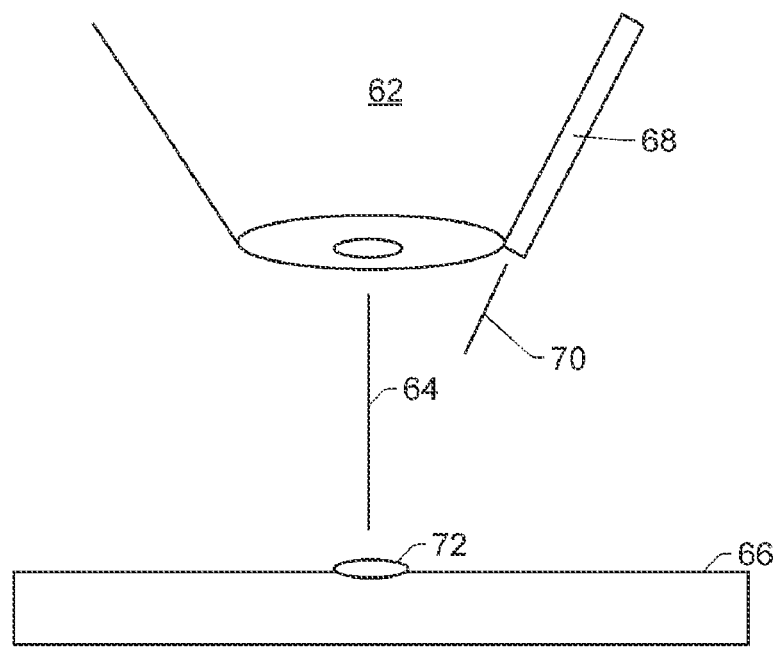

FIG. 9 illustrates another embodiment of a system that can be used to perform the methods described herein. As shown in FIG. 9, the system includes objective lens 62, which in combination with many other components (not shown) form an electron column of an electron delivery subsystem. The electron column is configured to generate electrons, which are then focused by objective lens 62 into electron beam 64. Electron beam 64 is directed to substrate 66. Substrate 66 is a copper containing substrate and may include any of the substrates described herein.

The system also includes chemical delivery subsystem 68. Chemical delivery subsystem 68 is configured to deliver one or more chemicals 70 to substrate 66. The one or more chemicals may include any of the etch chemistries described herein. For example, the one or more chemicals may be delivered to the substrate as a jet of halogen containing gas.

In this manner, the one or more chemicals may be delivered to the substrate in a relatively localized manner unlike the system shown in FIG. 8 in which the chemical(s) are delivered to the substrate in a global manner.

As shown in FIG. 9, the chemical delivery subsystem may be configured to deliver the one or more chemicals through a portion of objective lens 62. For example, one or more components of the chemical delivery subsystem such as tubing and a nozzle may be disposed within a portion of the objective lens. In this manner, the one or more chemicals may be delivered to the substrate in the vicinity of the outlet of the objective lens, and therefore in the vicinity of the electron beam. As such, the one or more chemicals may exit the chemical delivery subsystem relatively close to the targeted location on the substrate. However, it is to be understood that the chemical delivery subsystem and the electron delivery subsystem may be coupled in any other manner.

As further shown in FIG. 9, a portion of copper containing substrate 66 exposed to electron beam 64 will react with one or more chemicals 70 to form byproduct 72. For example, if the one or more chemicals include a chlorine containing compound, byproduct 72 may include copper chloride. The byproduct may be removed as described herein. The embodiment of the system shown in FIG. 9 may be further configured as described herein.

In the methods and systems described above, de-layering is accomplished with a combination of electrons and injected etchant gases at the substrate surface. Although de-layering using electron beam assisted chemical etching is a highly effective de-layering method, heating of the byproducts of the reaction can further accelerate the etching by facilitating the desorption of reaction byproducts at the surface of the substrate. For example, as further described herein, the byproducts of the reaction can be heated using light to assist the electron and etchant gas reactions. In particular, the portion of the copper structure that is being removed can be illuminated with light that is absorbed by a byproduct of the removal.

In one embodiment, a light beam may be used with the electron beam to assist in the etch reaction by heating the byproducts of the etch reaction. In particular, the light source may be selected such that the light has a wavelength that can be absorbed by the byproduct(s) of the reaction. The light may not be absorbed by the material being removed. In this manner, the material being removed may not be heated by the light source. Therefore, the wavelength may be selected to preferentially heat byproduct(s) that absorb light at that wavelength.

Figure 10:
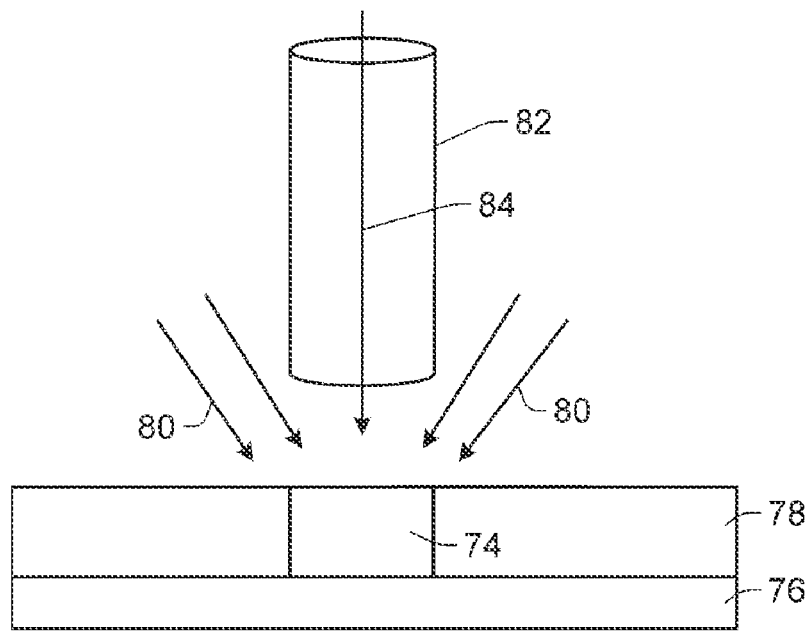
FIG. 10 is a schematic diagram illustrating a partial cross-sectional view of a copper structure on a substrate, which is exposed to chemical etching in combination with an electron beam and a light beam.
Figure 11:
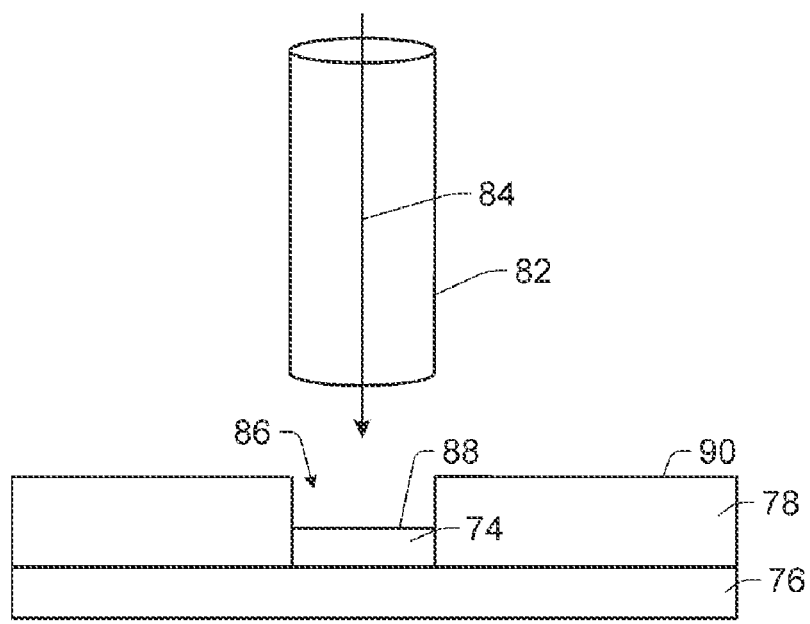
FIG. 11 is a schematic diagram illustrating a partial cross-sectional view of the substrate of FIG. 10 in which a portion of the copper structure is removed, and an electron beam and a light beam, both configured to perform analysis of the copper structure.

FIGS. 10–11 illustrate one embodiment of such a method for preparing a substrate for analysis. As shown in FIG. 10, copper structure 74 is formed on substrate 76. Substrate 76 may include any of the substrates described above. In this example, material 78 is formed on substrate 76. Copper structure 74 is formed in material 78. Material 78 may include any material known in the art such as an insulating material. Although only one material is shown on substrate 76 in FIGS. 10–11, it is to be understood that many materials may be formed on the substrates described herein. As shown in FIG. 10, copper structure 74 may be a patterned structure on the substrate. However, the copper structure may be an unpatterned copper layer as described above. As shown in FIG. 10, the substrate includes one copper structure. However, it is to be understood that the substrate may include more than one copper structure. The copper structures may be similarly or differently configured. The copper structures may be formed using any processes known in the art.

As shown in FIG. 10, a portion of copper structure 74 is exposed to etch chemistry 80 in combination with electron beam 82 and light beam 84. In some embodiments, the etch chemistry may include a chlorine-based chemistry, a bromine-based chemistry, or an iodine-based chemistry. These etch chemistries may include one or more chemicals. The selection of an etch chemistry may vary depending on, for example, the composition of copper structure 74 and the composition of any other materials on the substrate that might be exposed to the etch chemistry. The etch chemistry is preferably substantially inert with respect to the copper structure except in the presence of the electron beam. In other words, the etch chemistry will be "activated" to react with the portion of the copper structure that is exposed to the electron beam. In this manner, the etch chemistry will not etch other portions of the copper structure or other copper structures on the substrate (unless these other portions or structures are also exposed to the electron beam). Furthermore, the etch chemistry is preferably selected such that it does not substantially etch materials on the substrate other than copper structure. In this manner, the etch chemistry may not damage the substrate or other materials or features exposed to the etch chemistry. In addition, the selectivity of the de-layering process can be altered by changing one or more parameters of the electron beam and/or one or more parameters of the light beam.

As shown in FIG. 10, electron beam 82 is delivered to substrate 76 substantially coaxially with light beam 84. However, the light beam may not be delivered coaxially with the electron beam. The light and the electron beam may or may not be directed at the same time to the portion of the copper structure that is being removed. In addition, although the diameter of electron beam 82 is shown in FIG. 10 to be larger than the diameter of light beam 84, it is to be understood that a diameter of light beam 84 may be approximately equal to or greater than the diameter of electron beam 82. Light beam 84 may be generated by a laser (not shown). However, the light beam may be generated by any other appropriate light source known in the art. In general, light sources that are relatively bright at their operating wavelength(s) may be particularly useful in the methods described herein. One example of an appropriate laser is a Q-switched laser. Another example of an appropriate laser is a continuous wave (CW) laser.

The light source may also be a single wavelength laser or a multiple wavelength laser. In addition, the light beam may be generated using more than one light source. For example, light from several lasers may be combined into an optical train with a combiner. In this manner, not all of the different light beams may be delivered to the substrate at the same time.

The wavelength of light beam 84 will vary depending on the material that is being removed, the etch chemistry being used, and the byproducts that are formed between the material and the etch chemistry. For example, the wavelength of light beam 84 is preferably selected such that the light can be absorbed by the byproducts formed between the copper and the etch chemistry. In this manner, the light beam may heat the byproducts to facilitate desorption of the byproducts from the substrate. Such light accelerated desorption may be particularly advantageous for the methods described herein since the byproducts formed by such methods (e.g., $CuCl$, $CuCl_2$, $CuBr$, $CuBr_2$, or $CuI_2$) have substantially low volatility. For example, $CuCl$ is not volatile at room temperature. In addition, a wavelength or wavelengths of light may be used that is highly absorbed by the byproducts and highly reflected by the remaining or unreacted portions of the copper structure to reduce, and even minimize, collateral etching of the copper structure due to the light.

Examples of appropriate wavelengths of light for desorption of the byproducts described herein include 527 nm and 1053 nm. For example, the absorption coefficients for CuCl are about 5e-4 cm$^{-1}$ for 527 nm and about 1e-4 cm$^{-1}$ for 1053 nm, which are also available frequencies for high power CW and Q-switched YAG lasers. Reflectivity for copper is very high at these frequencies and drops many orders of magnitude in the blue and near ultraviolet (UV). Therefore, these relatively long wavelengths may be particularly suitable for the methods described herein.

The wavelengths which are used are determined based on the byproducts that will be formed, and if more than one byproduct is expected to be formed, more than one wavelength of light may be used for desorption. The removal of the byproduct(s) in such a manner during removal of the copper structure may also facilitate the rapid and efficient removal of the copper structure by preventing interference with the electron beam assisted etching by the byproduct(s).

As shown in FIG. 11, etch chemistry 80 in combination with electron beam 82 and light beam 84 removes portion 86 of copper structure 74. As further shown in FIG. 11, the remaining portion of the material proximate to the defect has upper surface 88 that is lower than upper surface 90 of material 78. Therefore, an entire thickness of the copper structure has not been removed. However, it is to be understood that the entire thickness of the copper structure may be removed in some embodiments. The depth to which the copper structure is removed may vary depending on, for example, the analysis that is to be performed on the structure.

The portion of the copper structure that is removed may be further configured as described above. For example, the portion of the copper structure that is removed may have an area that is approximately equal to the area of copper structure that is exposed to the electron beam. In one embodiment, the portion of the copper structure that is removed has an area that is equal to or less than about 10 μm by about 10 μm. Therefore, the area on the substrate in which the copper structure is removed is relatively small, particularly when compared to the amount of material that is typically removed by other de-layering processes. In this manner, the methods described herein may be performed on product wafers since in most instances removing material from such a small area on the product wafer will not adversely affect the product wafer as a whole. The area of the portion of the copper structure that is removed may be varied as described above. For example, the area of the copper structure that is removed is preferably kept at a minimum (to avoid damaging or destroying neighboring structures if present) while allowing analysis to be successfully completed.

The method may also include analyzing copper structure 74. The analysis may include any of the analysis described above. In one particular embodiment, as shown in FIG. 11, electron beam 82 that was used for removal may also be used to analyze structure 74. Parameters of the electron beam used for removal may be different than parameters of the electron beam that are used to analyze the structure. The analysis of the copper structure may include any of the analysis described above (e.g., imaging, composition determination, etc.). In addition, analysis using the electron beam may be performed during removal or after removal as described above.

Alternatively, or in addition, the copper structure may be analyzed with non-electron beam analysis. For example, an x-ray analysis system (not shown) may be used to analyze the copper structure as described further above. In other embodiments, light beam 84 may be used to analyze the copper structure. For example, the analysis may include inspection of the copper structure using the light. In another example, light beam 84 may be used to image the copper structure. The image of the copper structure may then be used to determine one or more characteristics of the copper structure. The light may also be used to determine a characteristic of a defect detected by inspection performed using the light.

Parameters of the light beam may be changed between removal and analysis. For example, a wavelength and/or a polarization of the light beam may be changed after de-layering but before analysis of the copper structure is performed. Other parameters of light beam 84 may be similarly altered between removal and analysis. In another embodiment, light beam 84 may be used to image the structure as the material is being removed. In this manner, the de-layering process can be monitored and recorded, which may provide further information about the structure and the de-layering process. This information can be used to monitor and/or control the de-layering process as described further herein. In other embodiments, a different light beam may be used to analyze the structure as described herein. This light beam may or may not be coaxial with electron beam 82.

FIGS. 12–14 illustrate scanning electron microscope (SEM) images of substrates that include copper structures processed as described herein. The copper structures on the substrates shown in FIGS. 12–14 are unpatterned copper layers. The SEM image shown in FIG. 12 illustrates copper removal using a CW mode laser having a wavelength of 1053 nm and a power of 200 mW. The laser was used in combination with an electron beam having the following parameters: current=5 nA, energy 5 kV. In addition, the laser and electron beam were used in combination with a gas that included 0.1 sccm $Cl_2$. A 15 minute etch was performed in a field of view of about 80 μm on the copper layer. As shown in FIG. 12, the use of the laser allowed more reacted material (the byproduct between copper layer 92 and the etch chemistry in the presence of the electron beam) to be removed particularly in comparison to the SEM images of FIGS. 5–7. As shown in FIG. 12, area 94 of the removed reacted material is again substantially limited to the area of the copper layer that was exposed to the electron beam.

FIGS. 13 and 14 illustrate at different magnifications another substrate that includes copper layer 96, a portion of which was removed using an etch chemistry in combination with an electron beam. The etch chemistry used for removal was 0.1 sccm chlorine gas ($Cl_2$). The electron beam had a 5 nA beam current and was used in spot mode. As shown in FIGS. 13 and 14, area 98 of copper layer 96 that is removed is substantially limited to the area of the copper layer that was exposed to the electron beam. The substrate was also exposed to a laser beam to facilitate removal of the byproduct of the reaction between the copper layer and the etch chemistry. The laser that was used for byproduct desorption was a 0.6 Acm$^{-2}$ laser (Q-switched to 3 kHz) having a wavelength of 1053 nm and a power of 540 Wcm$^{-2}$. As shown in FIGS. 13 and 14, the laser flux caused substantially no collateral etch or edge deposition on the remaining portions of the copper structure.

As with the SEM images shown in FIGS. 5–7, the above described examples are merely intended to illustrate the capability of the methods and systems described herein and are not intended to be limiting examples of the present invention. In particular, the images shown in FIGS. 12–14 illustrate that light can be used to facilitate removal of reaction byproducts from the substrate surface. Therefore, although the methods and systems described herein may form relatively non-volatile byproducts during removal, these byproducts can be efficiently removed with little difficulty. In addition, the images shown in FIGS. 13 and 14 illustrate that a relatively small area of the copper layer may be removed using the methods described herein. In particular, an area of less than about 10 µm by about 10 µm of the copper layer was removed as shown in FIG. 13. In addition, as shown in FIG. 14, the area of the copper layer that was removed was about 1 µm by about 1 µm. Therefore, these images illustrate that the methods and systems described herein can be used for truly localized reaction and removal of copper structures on a substrate.

Figure 15:
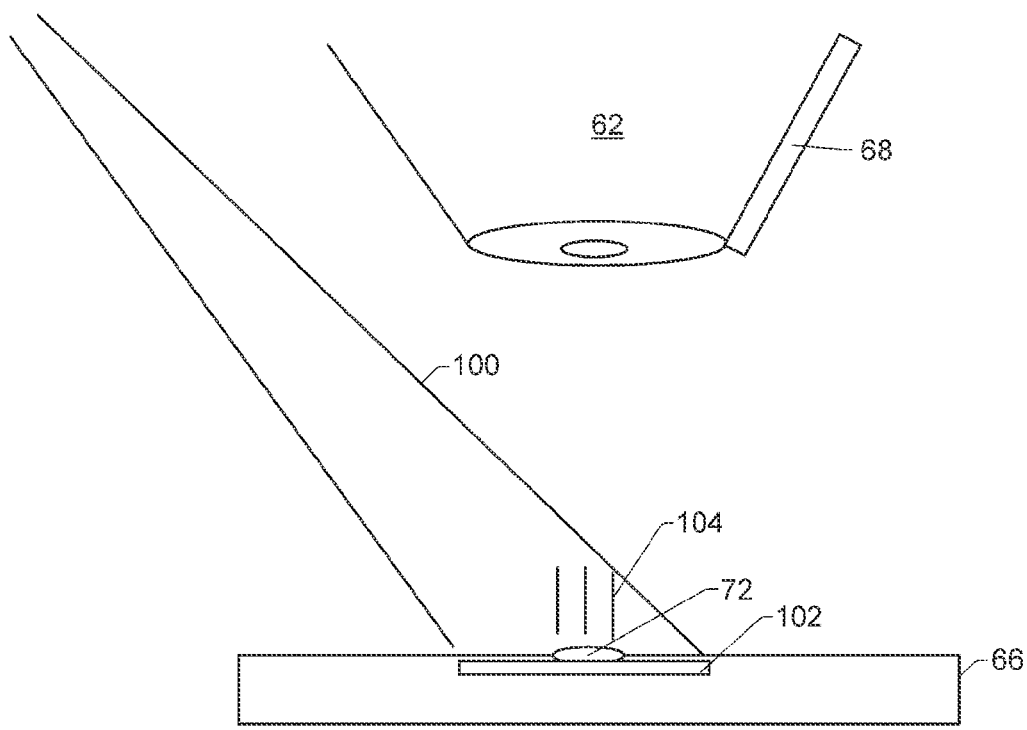
FIGS. 15–16 are schematic diagrams illustrating partial cross-sectional views of different systems configured to prepare a substrate for analysis.

FIG. 15 illustrates one example of a system that can be used to perform the methods described herein. The system shown in FIG. 15 is much like that shown in FIG. 9 except for the additional capabilities of the system shown in FIG. 15. For example, the system shown in FIG. 15 includes objective lens 62 and chemical delivery subsystem 68, which may be configured as described above. As shown in FIG. 15, an electron beam from the objective lens in combination with one or more chemicals from the chemical delivery subsystem were used to create byproduct 72 on the surface of copper containing substrate 66.

As further shown in FIG. 15, the system is configured to direct light 100 to substrate 66. In particular, the system may include a light delivery subsystem (not shown), which may be configured as described herein, to deliver light to the portion of the copper structure being removed. The light delivery subsystem may include a laser that is configured to generate light 100 having a wavelength of about 527 nm or about 1053 nm. As shown in FIG. 15, the light beam will not be coaxial with the electron beam from objective lens 62. However, it is to be understood that the system shown in FIG. 15 may be configured as described further herein such that the light beam and the electron beam may be delivered substantially coaxially to the substrate. In addition, the electron delivery subsystem and the light delivery subsystem may be configured to deliver the light and the electron beam to the portion of the copper structure at the same time.

The light may illuminate area 102 on substrate 66, which may be larger than an area of byproduct 72. Area 102 illuminated by light 100 may have any suitable dimensions, but preferably the area of the light on the substrate is larger than an area of byproduct 72 such that the byproduct may be completely illuminated. Preferably, light 100 is absorbed by byproduct 72 such that the byproduct is heated thereby facilitating desorption 104 of the byproduct from the substrate. The system shown in FIG. 15 may be further configured as described herein. For example, the system may be configured to perform analysis of the copper structure using the light delivery subsystem to inspect the copper structure. In another example, the system may be configured to perform analysis using the light delivery subsystem to determine a characteristic of a defect in the copper structure.

Figure 16:
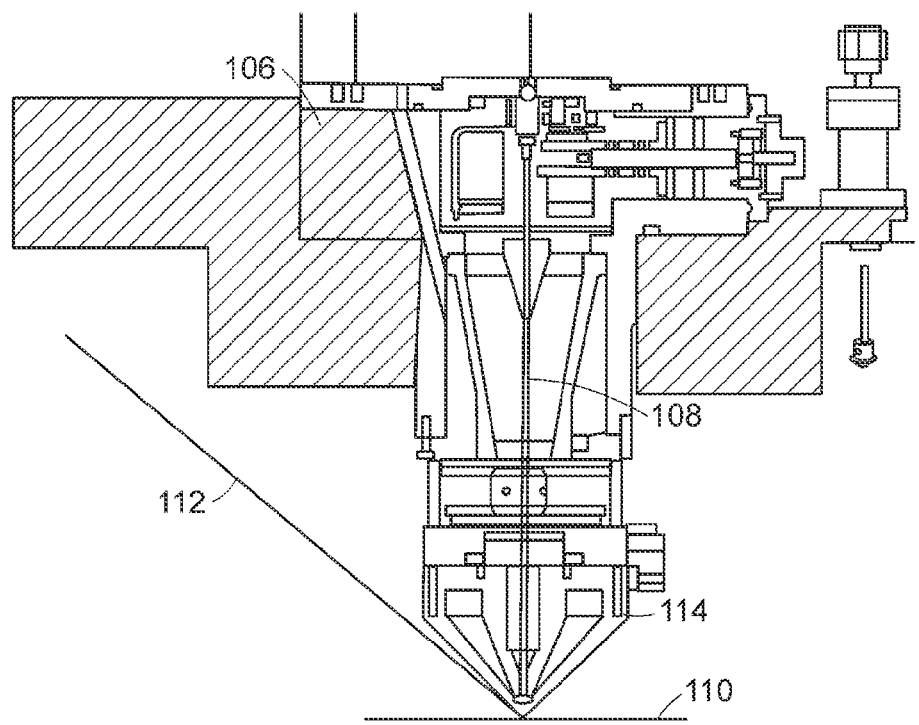

FIG. 16 illustrates one example of a system that is configured to prepare a substrate for analysis. In this example, the system includes electron delivery subsystem 106. Electron delivery subsystem 106 is configured as an electron column. The electron delivery subsystem is configured to deliver electron beam 108 to substrate 110. As shown in FIG. 16, the system is also configured to deliver light beam 112 to substrate 110. Light beam 112 and electron beam 108 are delivered to approximately the same spot on substrate 110. The system shown in FIG. 16 also includes a chemical delivery subsystem (not shown) that is configured to deliver one or more chemicals (not shown) to substrate 110. The one or more chemicals in combination with electron beam 108 and light beam 112 remove a portion of a copper structure (not shown) on the substrate.

Figure 17:
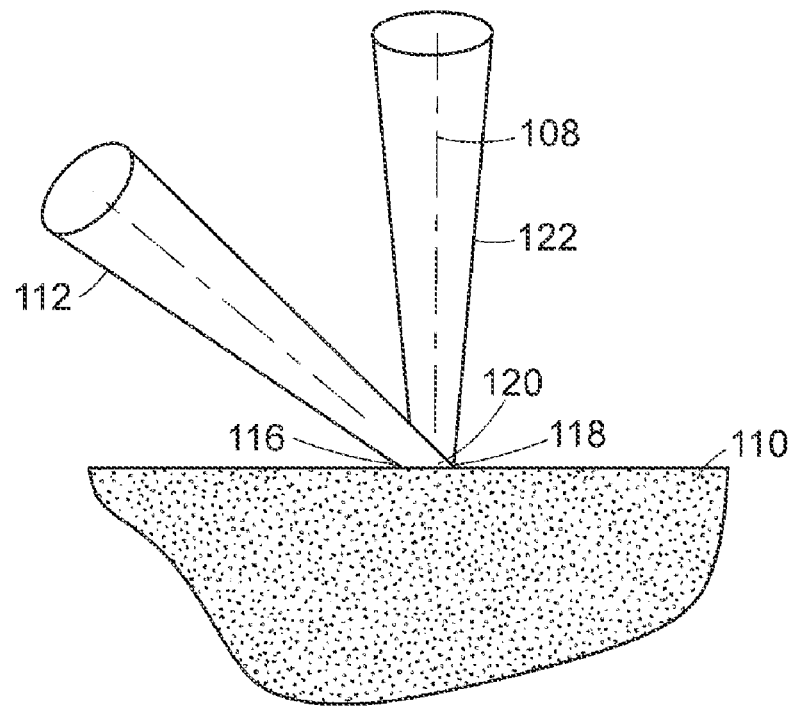
FIG. 17 is a schematic diagram illustrating a side view of focal spots on a substrate by off-axis and coaxial laser delivery.

As shown in FIG. 16, light beam 112 is delivered to the substrate by focusing the beam at a glancing angle that is tangential to the outside edge of objective lens 114 of the electron delivery subsystem. In this manner, the light beam is off-axis with respect to the electron beam. In other words, the light beam is not delivered to the substrate coaxially with the electron beam. This configuration allows the light beam to be focused on the substrate without any modifications to the electron column. However, because the light beam is focused at a glancing angle (about 55° from the vertical), the intersection point of the electron beam focus, the light beam focus and the substrate is critically dependent on the striking distance (i.e., the separation of the objective lens and the substrate). Any change in the working distance would cause the laser beam to overshoot or undershoot the axial point, necessitating a re-alignment of the light beam. In addition, as shown in FIG. 17, because light beam 112 lands on substrate 110 at a glancing angle, focal spot 116 of light beam 112 is an ellipse smeared out in the major diameter by a factor of about 1.74, while focal spot 118 of electron beam 108 is circular. Also, reflectance 120 of the surface at the glancing angle decreases the amount of energy delivered to the process by the light beam.

Delivering the light beam to the substrate coaxially with the electron beam eliminates the problems outlined above. As shown in FIG. 17, when light beam 122 is delivered to substrate 110 coaxially with electron beam 108, the focal spots of both beams are circular. In addition, the focal spot of light beam 122 will be substantially uniform. Therefore, the electron beam focus, the light beam focus, and the substrate will not be critically dependent on the separation of the objective lens and the substrate. In this manner, alignment of the light beam is not critically dependent on the working distance. As such, changes in the working distance will not require re-alignment of light beam 122. Therefore, the systems described further herein will be easier to operate than non-coaxial systems. Furthermore, delivering light beam 122 to substrate 110 at a substantially normal angle will reduce reflectance of the light beam from the surface of the substrate. Consequently, the systems described further herein will have improved delivery of light energy to the de-layering process.

Figure 18:
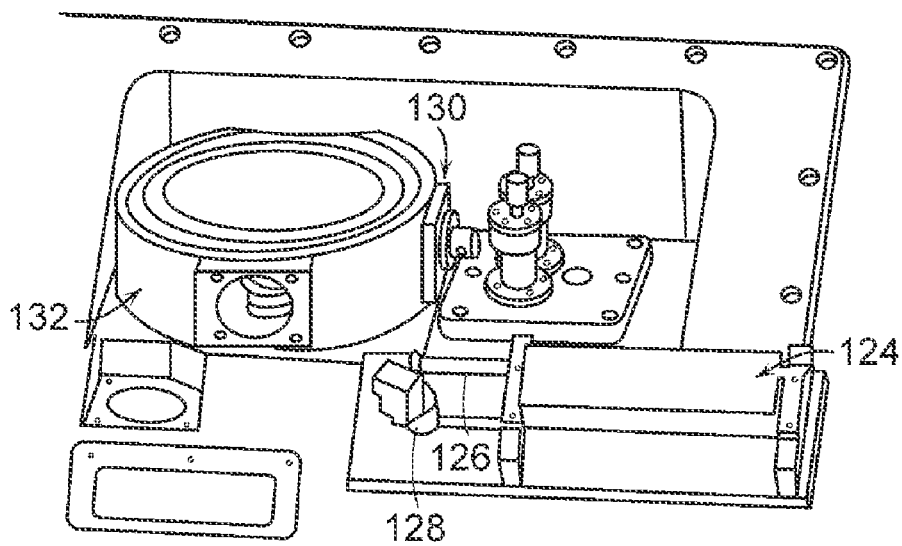
FIG. 18 is a schematic diagram illustrating a perspective top view of one embodiment of a portion of a system configured to prepare a substrate for analysis.
Figure 19:
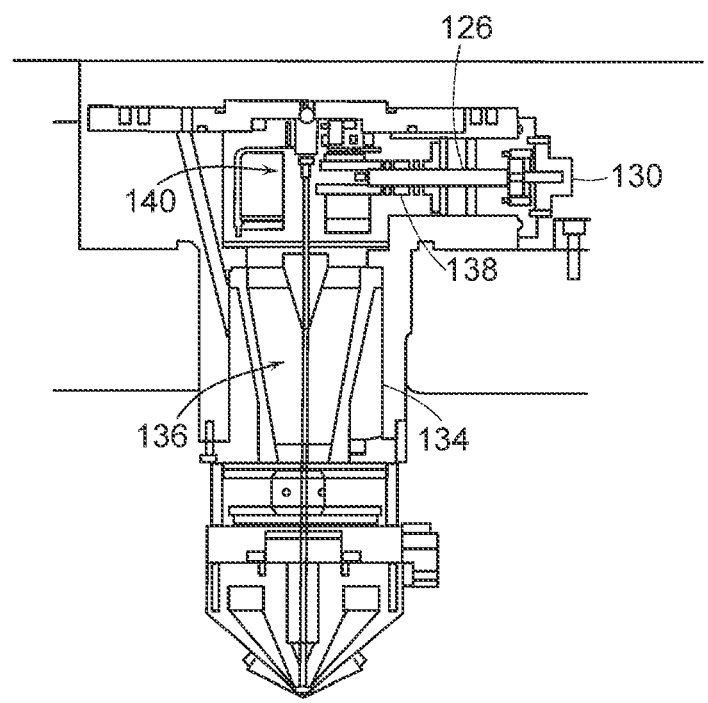
FIG. 19 is a schematic diagram illustrating a partial cross-sectional view of an embodiment of a portion of a system configured to prepare a substrate for analysis.

FIGS. 18 and 19 illustrate one embodiment of an electron and light delivery subsystem that may be included in a system configured to prepare a substrate for analysis. The electron and light delivery subsystem is configured to illuminate the field of view of an electron beam with light or laser energy focused to a relatively small spot diameter. Therefore, the system is configured to enhance the de-layering process by heating any byproducts to facilitate desorption of the byproducts from the substrate. As shown in FIG. 18, the electron and light delivery subsystem includes light source 124. Light source 124 is configured to generate light beam 126. Light beam 126 is directed by optical component 128 to optical window 130 in column base 132 of an electron column of the electron and light delivery subsystem. The optical window may be configured as a vacuum window. The optical window is configured to allow light beam 126 to enter the electron column.

As shown in FIG. 19, electron column 134 is configured to deliver electron beam 136 to a substrate (not shown). After entering electron column 134 through optical window 130, light beam 126 is focused to a spot (e.g., by a simple lens (not shown)), and this image is focused by lens 138 to mirror 140 and eventually to the substrate. Lens 138 may be a long focal length transfer lens or any other appropriate lens known in the art. Light beam 126 is reflected from mirror 140. Mirror 140 may be a 45° metallic mirror. Mirror 140 may also be a convolving laser mirror. Mirror 140 has an aperture (not shown) formed through the mirror. Preferably, the aperture is configured to allow electron beam 136 to pass through the aperture. For example, the aperture may be centered in the mirror and may have a diameter of about 1 mm. In addition, the mirror is preferably placed axially in the electron column with the aperture lined up with the axis of electron beam 136. In this manner, the electron beam can follow its axial path through the electron column and through the aperture in mirror 140. Therefore, after being reflected from mirror 140, light beam 126 will be coaxial with electron beam 136. In this manner, the electron and light delivery subsystem is configured to deliver electron beam 136 to the substrate coaxially with light beam 126. Although there will be a slight loss of light beam power (e.g., about 5%) due to the aperture in the center of the mirror, such a loss is acceptable and will not diminish the functionality of the electron and light delivery subsystem.

The electron and light delivery subsystem shown in FIGS. 18 and 19 is included in a system along with a chemical delivery subsystem (not shown) that is configured to delivery one or more chemicals to a substrate. The chemical delivery subsystem may be configured as described above. The one or more chemicals in combination with electron beam 136 and light beam 126 remove a portion of a copper structure on the substrate, as shown in FIGS. 10 and 11. The portion of the copper structure that is removed may have an area that is equal to or less than about 10 µm by about 10 µm, as described above. As further described above, the area of the portion of the copper structure that is removed may vary depending on, for example, parameters of the electron beam.

Light source 124 may be a laser. Light source 124 may be configured as described above. For example, the wavelength of light beam 126 will vary depending on the material that is being removed, the etch chemistry that is being used, and the byproducts formed thereof. For example, depending on the material being removed, the wavelength of light beam 126 is selected such that the light can be absorbed by the byproducts of removal. In this manner, the electron and light delivery subsystem may be configured such that light beam 126 heats a byproduct on the substrate as described above. In addition, the light beam may have one wavelength (e.g., monochromatic light), approximately one wavelength (e.g., near monochromatic light), or more than one wavelength of light (e.g., polychromatic light or broadband light).

The systems shown in FIGS. 15–16 and 18–19 may be further configured as described herein. For example, the system shown in FIGS. 18–19 may be configured to use electron beam 136 and/or light beam 126 to perform analysis of the copper structure. In addition, the system may include an analysis subsystem that is configured to perform analysis of the copper structure. The analysis subsystem may be configured as described herein.

In another embodiment, the one or more chemicals that are delivered to the substrate during the removal process may include an oxygen containing compound such as oxygen gas ($O_2$). In some embodiments, the oxygen containing compound may be included in the one or more chemicals that are delivered to the substrate to improve the side wall definition. In some embodiments, the one or more chemicals may include $O_2$ and chlorine gas ($Cl_2$). The ratio of $O_2$ to $Cl_2$ and the total gas flow may be varied to determine the optimal setting for best edge definition and etch consistency. By one set of experiments, the ideal ratio of $O_2$ to $Cl_2$ was found to be 1.00 sccm $O_2$, 0.1 sccm $Cl_2$ through a needle valve that was 4 turns open (uncalibrated). Of course, the appropriate or optimal ratio may vary depending on the chemicals that are used and characteristics of the substrate on which copper structures are being removed.

Figure 20:
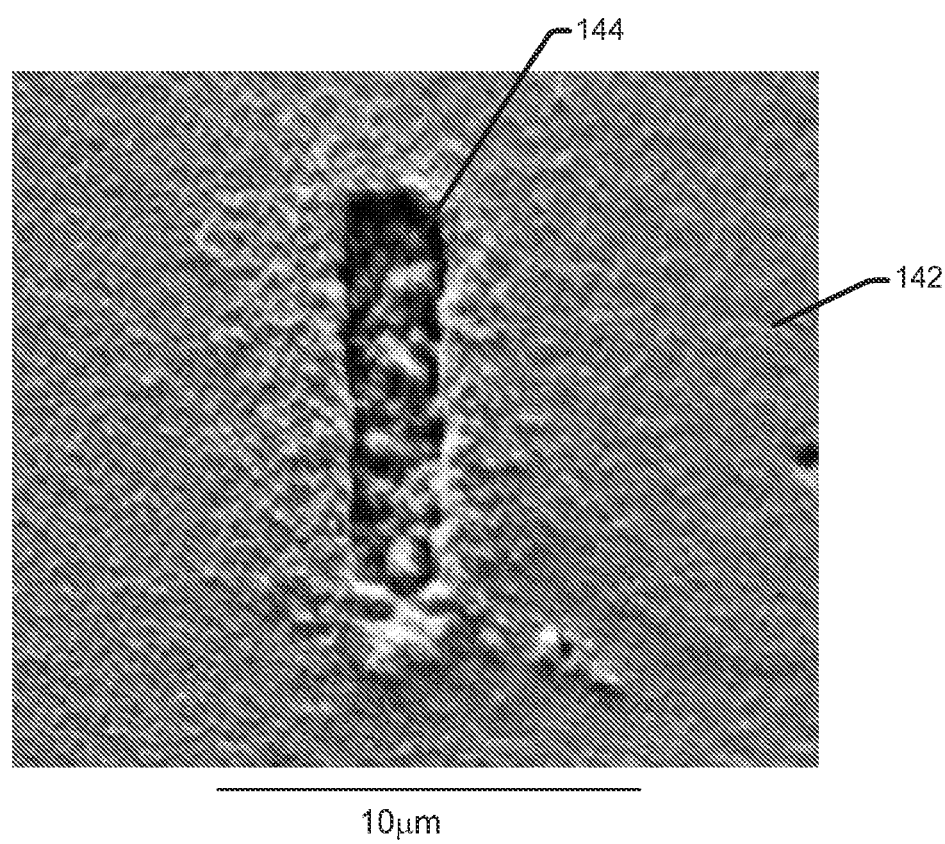
FIG. 20 is a SEM image of a copper layer formed on a substrate, a portion of which was removed using an etch chemistry, which includes an oxygen containing compound, in combination with an electron beam and a light beam.

FIG. 20 illustrates one example of a substrate that includes copper layer 142, which was processed according to the methods described herein in combination with an oxygen containing compound. In particular, a gas that included 1.00 sccm $O_2$ and 0.1 sccm $Cl_2$ was introduced into a chamber in which the substrate was disposed through a needle valve that was four turns open (uncalibrated). A 5 minute etch was performed using a low energy (LE) electron beam having the following parameters: current=5 nA, energy=2 kV. A light source was used to facilitate the removal of any byproducts that were formed. The light source was a laser (Q-switched to 1.5 kHz) having a wavelength of 1053 nm and a power of 537 Wcm$^{-2}$.

As shown in FIG. 20, area 144 of the removed portion of the copper layer is substantially limited to the area that was exposed to the electron beam. In addition, as shown in FIG. 20, the area of the copper layer that was removed is less than about 10 µm by about 10 µm. Furthermore, the remaining portion of the copper layer surrounding the removed portion of area 144 has a relatively good sidewall profile. The sidewall profile of the remaining portion of the copper layer surrounding the removed portion may have been improved, in comparison with other images illustrated herein, in large part due to the presence of the oxygen gas in the process chamber. As with the SEM images shown in FIGS. 5–7 and 12–14, the above described example is merely intended to illustrate the capability of the methods and systems described herein and is not intended to be a limiting example of the present invention.

The methods described above may also or alternatively include removing from the substrate a byproduct of the copper structure removal using one or more chemicals. The one or more chemicals selected for byproduct removal may include an oxygen containing compound such as oxygen gas ($O_2$). For example, in some embodiments, etchant precursors may be used that are substantially inert and may deposit carbon such as carbon tetrachloride ($CCl_4$) in combination with $O_2$ or other oxygen containing compounds such as water vapor to remove carbon containing byproducts from the substrate. In this manner, carbon containing reaction byproducts caused by carbon containing precursors in etch chemistries such as $CCl_4$ and tetrachloroethene ($C_2Cl_4$) can be removed to prevent blocking or inhibition of the removal process in one or more regions on the substrate. In some embodiments, the chemicals may produce carbon monoxide (CO), carbon dioxide ($CO_2$), or some carbon, oxygen, and chlorine containing volatile compound such as phosgene ($COCl_2$) or other volatile product(s) at the surface of the substrate under the electron beam, which can then be easily removed.

In another embodiment, the one or more chemicals may include xenon difluoride ($XeF_2$). For example, in one embodiment, the chlorine-based chemistry may include silicon tetrachloride ($SiCl_4$). In this embodiment, the chlorine-based chemistry may deposit silicon byproducts on the surface of the substrate. $XeF_2$ may be used to remove any silicon buildup on the surface of the substrate. In a different embodiment, the one or more chemicals may include tetraethyl phosphine ($PEt_3$). For example, a transport agent such as $PEt_3$ may be used to facilitate removal of CuCl and/or other halogen products from the surface of the specimen. Such chemical(s) may be delivered to the portion of the copper structure for byproduct removal by any of the chemical delivery subsystems described herein.

In addition, the etch chemistry may include $CCl_4$ or $SiCl_4$ as described above, which can also be substituted with a longer chain molecule of similar composition such as $C_2Cl_6$, $Si_2Cl_6$ or any other chlorine containing trimer, tetramer, etc. of carbon or silicon.

Another method for preparing a substrate for analysis includes exposing the substrate to a fluorine containing chemical. The fluorine containing chemical bonds to the substrate to form a fluorine containing layer on the substrate. The fluorine containing chemical may include any of those described herein such as xenon difluoride ($XeF_2$). In addition, the exposing step may be performed with more than one fluorine containing chemical or with a combination of fluorine containing chemical(s) and non-fluorine containing chemical(s).

The method also includes removing copper in a first portion of the substrate by directing an electron beam to the first portion in the presence of an etch chemistry. Other portions of the substrate not exposed to the electron beam are not removed due to the fluorine containing layer. In this manner, the fluorine containing layer may act as a passivation layer or mask to protect some portion of the substrate from etching. For example, the etch chemistry may include a chlorine-based etch chemistry including any of the chemistries described herein such as chlorine gas. Since the Cu—F bond is stronger than the Cu—Cl or other halogen bond, the areas bonded to fluorine will be masked from removal by the etch chemistry. This method may be performed using any of the systems described herein.

In some embodiments, the method may also include prior to the exposing step, cleaning the substrate to remove oxide present on the substrate. In this manner, if any oxide is present on the substrate, it can be removed such that the oxide does not interfere with formation of the fluorine containing layer on the substrate. The oxide can be removed using any suitable processes known in the art. In addition, the oxide can be removed using any of the systems described herein, for example, by providing the appropriate chemical(s) for oxide removal using the chemical delivery subsystem.

In one embodiment, during exposure of the substrate to the fluorine containing chemical, the electron beam may be directed to the substrate. The electron beam may facilitate the formation of the fluorine containing layer on the substrate by "activating" the fluorine containing chemical or by "activating" the substrate surface. For instance, the fluorine containing chemical may be substantially inert with respect to the substrate except in the presence of the electron beam. One example of such a substantially inert fluorine containing chemical is carbon tetrafluoride ($CF_4$), which can be rendered active by exposure to the electron beam. In this manner, the electron beam may be directed to select locations on the substrate, and the fluorine containing layer will be formed on only those locations that are illuminated by the electron beam. As such, the fluorine containing layer may be "written" on the substrate using the electron beam.

Figure 21:
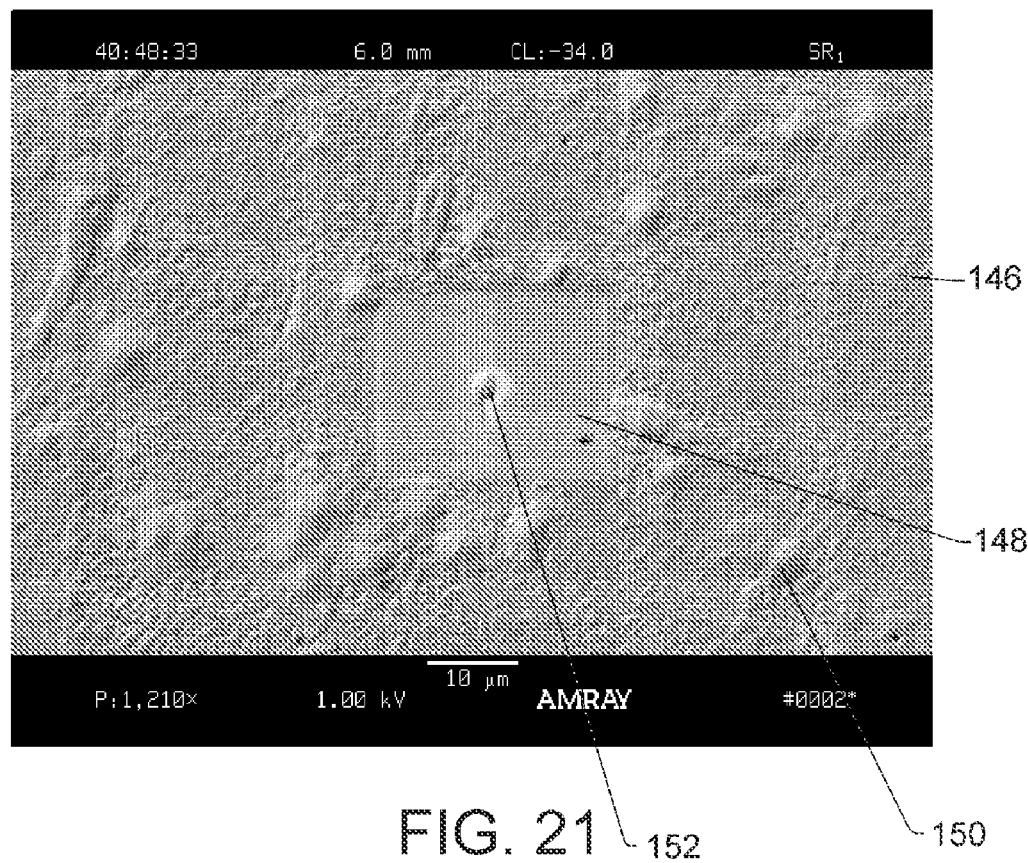
FIG. 21 is a SEM image of a copper layer including an area that was exposed to an electron beam and a fluorine containing chemical prior to removal of copper in a portion of the area using an etch chemistry in combination with an electron beam.

A substrate that was processed using the method described above is illustrated in FIG. 21. FIG. 21 is a SEM image of a substrate that includes a copper layer, a portion of which was removed as described below. Copper layer 146 includes area 148, which was exposed to an electron beam and a fluorine containing chemical. The fluorine containing chemical used in this example was xenon difluoride ($XeF_2$). The fluorine containing chemical although generally inert with respect to the copper layer was "activated" by the electron beam such that a fluorine containing layer was formed on the area of the copper layer that was illuminated by the electron beam. The fluorine containing layer acts as a passivation layer in that during further exposure of the substrate to etch chemistries, the portion of the copper layer on which the fluorine containing chemical was formed will not be removed.

For instance, as shown in FIG. 21, the substrate was exposed to a chlorine-based chemistry, particularly chlorine gas, and area 150 surrounding passivated area 148 reacted with the chlorine-based chemistry. However, area 148 did not react with the chlorine-based chemistry except in area 152 of the passivated area, which was exposed to an electron beam during the exposure of the substrate to the chlorine-based chemistry. The reaction between the copper layer and the chlorine gas most likely resulted in the formation of copper chloride to which the roughness of the copper layer except in area 148 can be attributed. The copper chloride can be removed as described herein (e.g., using light).

As with other SEM images present herein, the SEM image shown in FIG. 21 is presented herein to merely illustrate the capability and advantages of the embodiments of the methods and systems described herein, and is not intended to be a limiting embodiment. For instance, the SEM image shown in FIG. 21 illustrates that a fluorine containing layer can be formed in an area on a copper structure defined by an electron beam. In addition, the SEM image of FIG. 21 illustrates that the fluorine containing layer will protect underlying portions of the copper structure from removal by another etch chemistry. Furthermore, the SEM image of FIG. 21 illustrates that the fluorine containing layer can be etched through using an etch chemistry that is activated by an electron beam. In other words, an electron beam can be used during chlorine exposure of the substrate to "activate" areas that have been inhibited with fluorine. In this manner, substantially an entire copper structure may be passivated by such a fluorine containing layer, and portions which are to be analyzed may be removed by the methods described herein. In this manner, the methods described herein can be used for truly localized removal of a copper structure, as shown in FIG. 21.

In addition, in methods in which a protective passivation layer is formed on the copper structure, the etch chemistry that is used to remove a portion of the copper structure in a localized manner may or may not be substantially inert with respect to the copper structure except in the presence of the electron beam. In other words, since the passivation layer will reduce etching of the copper structure underlying the passivation layer, the etch chemistry that is used for etching may be more reactive with the copper structure. In this manner, the methods involving the formation of the fluorine containing layer may substantially increase the number of etch chemistries that can be used in the methods.

In a different embodiment, prior to exposing the substrate to the fluorine containing chemical, the electron beam may be directed to the substrate to prepare the substrate for bonding with the fluorine containing chemical. For example, the electron beam may "activate" the surface of the substrate such that portions of the substrate that were exposed to the electron beam will react with the fluorine containing chemical. In these embodiments, the fluorine containing chemical may or may not be substantially inert with respect to the substrate.

Figure 22:
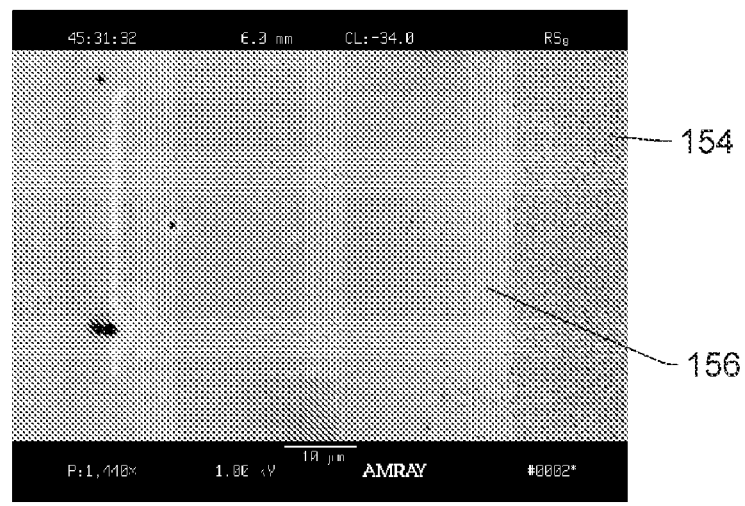
FIG. 22 is a SEM image of a copper layer including an area that was exposed to an electron beam and then a fluorine containing chemical prior to removal of a portion of the copper layer surrounding the area, which is performed using an etch chemistry.

A substrate that was processed using the method described above is illustrated in FIG. 22. FIG. 22 is a SEM image of a substrate that includes a copper layer, a portion of which was removed as described below. Copper layer 154 includes area 156, which was exposed to an electron beam. The substrate was then exposed to a fluorine containing chemical. The fluorine containing chemical used in this example was xenon difluoride ($XeF_2$). The area that was exposed to the electron beam is effectively prepared or "activated" to react with the fluorine containing chemical. The fluorine containing chemical reacted with the portion of the copper layer that was exposed to the electron beam to form a fluorine containing layer on area 156. The fluorine containing layer serves as a passivation layer such that portions of the copper structure underlying the fluorine containing layer are not removed during exposure to other chemicals.

In particular, after the fluorine containing layer is formed in area 156, the substrate was exposed to a chlorine-based etch chemistry. The etch chemistry in this example included chlorine gas. As shown in FIG. 22, areas of the copper layer other than area 156 reacted with the chlorine gas. The reaction between the copper layer and the chlorine gas most likely resulted in the formation of copper chloride to which the roughness of the copper layer except in area 156 can be attributed. The copper chloride can be removed as described herein (e.g., using light).

As with other SEM images present herein, the SEM image shown in FIG. 22 is presented herein to merely illustrate the capability and advantages of the embodiments of the methods and systems described herein, and is not intended to be a limiting example. For instance, the SEM image shown in FIG. 22 illustrates that a fluorine containing layer can be formed in an area on a copper structure predefined by an electron beam. In addition, the SEM image of FIG. 22 illustrates that the fluorine containing layer will protect underlying portions of the copper structure from removal by another etch chemistry. In this manner, such fluorine containing layers can be used in the methods described herein for truly localized removal of a copper structure. In addition, in methods where a protective passivation layer is formed on the copper structure, the etch chemistry that is used to remove a portion of the copper structure in a localized manner may or may not be substantially inert with respect to the copper structure except in the presence of the electron beam, as described above.

Any of the fluorine containing masking layers described above may be removed after the localized etching step using any process known in the art. In addition, although use of the fluorine containing masking layers is described herein with respect to copper structures, it is to be understood that such fluorine containing masking layers may be used in the same manner described herein for other materials. Determination of such other materials is well within the skill of one of ordinary skill in the art and may involve routine experimentation that can be performed using the description provided herein as a guide for such experimentation.

The fluorine containing layer may be selectively formed on areas of the substrate that are pre-activated by the electron beam or that are activated during exposure to the fluorine containing chemical(s). In one particular embodiment, a method for preparing a substrate for analysis may include exposing a first portion of the substrate to an electron beam. A second portion of the substrate not exposed to the electron beam includes a copper structure. The method also include exposing the substrate to a fluorine containing chemical. The fluorine containing chemical may include any of those described herein such as xenon difluoride ($XeF_2$) and possibly other chemicals such as carbon tetrafluoride ($CF_4$). The fluorine containing chemical bonds to the first portion but not the second portion to form a fluorine containing layer on the first portion.

In this manner, at least a portion of a copper structure may be located in the second portion such that at least the portion of the copper structure can be subsequently removed. It is noted that the first portion of the substrate that is protected from removal by the fluorine containing layer may also include copper. For example, the first portion may include one or more additional copper structures. In addition, or alternatively, the first portion may include an additional portion of the copper structure present in the second portion. In other words, one copper structure may be included in both the first and second portions of the substrate when only a portion of the copper structure is to be removed.

Subsequent to forming the fluorine containing layer on at least the first portion of the substrate, the method may include exposing the substrate to an etch chemistry. The etch chemistry does not etch the first portion of the substrate due to the fluorine containing layer. The etch chemistry does, however, etch the copper structure in the second portion of the substrate. The etch chemistry may include any of the etch chemistries described herein such as a chlorine-based chemistry. In these embodiments, the etch chemistry may or may not be substantially inert with respect to the copper structure since even if the chemistry is relatively reactive with respect to copper, portions which are not to be removed will be protected by the fluorine containing layer. The methods described above may also be performed using the systems described herein.

In the embodiments described above, the methods include forming a fluorine containing masking layer on a substrate and then removing a portion of a copper structure on the substrate. However, in another embodiment, the substrate may be exposed to a fluorine containing chemical during removal of the portion of the copper structure to effectively inhibit the removal of other portions of the copper structure and/or other copper structures on the substrate. In this manner, the fluorine containing layer may not be formed on the substrate prior to exposing the substrate to the etch chemistry.

One such embodiment of a method for preparing a substrate for analysis includes removing a portion of a copper structure on the substrate using an etch chemistry in combination with an electron beam. The etch chemistry is substantially inert with respect to the copper structure except in the presence of the electron beam. Therefore, this step may be performed as described in detail above using any of the etch chemistries described herein. For example, the etch chemistry may include a chlorine-based chemistry.

The method also includes inhibiting removal of other portions of the copper structure and other copper structures on the substrate during the removing step by exposing the substrate to a fluorine containing chemical during the removing step. The fluorine containing chemical bonds with the other portions of the copper structure and the other copper structures on the substrate. The fluorine containing chemical may include any of the fluorine containing chemicals described herein such as xenon difluoride ($XeF_2$). In addition, the substrate may be exposed to more than one fluorine containing chemical during the removing step. In another example, the substrate may be exposed to a combination of fluorine and non-fluorine containing chemicals during the removing step. The embodiments of this method may also be performed using one of the systems described herein.

In all cases described herein, etching will occur only in the desired area, which can be defined either by the electron beam or by a fluorine containing mask that may be formed with the aid of an electron beam. In addition, the embodiments described above in which the portions of the substrate not to be etched or removed are masked with a fluorine containing layer may be altered such that the masking is performed with an oxygen containing layer such as an oxide or a carbon containing layer. For example, the chemicals that are used to form the fluorine containing layer on the substrate may be changed such that the composition of the masking layer is different. These layers may provide protection for underlying layers that is similar to the protection provided by the fluorine containing layers. In addition, after selective removal of portions of the substrate, these layers can be removed using any processes known in the art such as cleaning, etching, or stripping processes.

Further modifications and alternative embodiments of various aspects of the invention may be apparent to those skilled in the art in view of this description. For example, methods and systems for preparing a copper containing substrate for analysis are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for preparing a substrate for analysis, comprising:
    removing a portion of a copper structure on the substrate using an etch chemistry in combination with an electron beam, wherein the etch chemistry is substantially inert with respect to the copper structure except in the presence of the electron beam;
    illuminating the portion of the copper structure with light that is absorbed by a byproduct of said removing; and
    performing the analysis, wherein the analysis comprises inspection of the copper structure using the light.

2. The method of claim 1, wherein the etch chemistry comprises a chlorine-based chemistry.

3. The method of claim 1, wherein the portion of the copper structure has an area that is equal to or less than about 10 µm by about 10 µm.

4. The method of claim 1, wherein the portion of the copper structure has an area that is approximately equal to an area of the electron beam on the copper structure.

5. The method of claim 1, wherein the light is substantially coaxial with the electron beam.

6. The method of claim 1, wherein the light and the electron beam are directed to the portion of the copper structure at the same time.

7. The method of claim 1, wherein the analysis further comprises determination of a characteristic of a defect detected by the inspection.

8. The method of claim 1, further comprising removing from the substrate the byproduct of said removing using one or more chemicals.

9. The method of claim 8, wherein the one or more chemicals comprise an oxygen containing compound.

10. The method of claim 8, wherein the one or more chemicals comprise xenon difluoride.

11. The method of claim 8, wherein the one or more chemicals comprise tetraethyl phosphine.

12. The method of claim 1, wherein the substrate comprises a patterned wafer.

13. The method of claim 1, wherein the analysis further comprises inspection of the copper structure using the electron beam.

14. The method of claim 1, wherein the analysis further comprises inspection of the copper structure using the electron beam and determination of a characteristic of a defect detected by the inspection using the electron beam.

15. The method of claim 1, wherein the inspection comprises inspection of the copper structure for subsurface or partially subsurface defects.

16. The method of claim 1, wherein the analysis further comprises root cause analysis of defects detected by the inspection.

17. A method for preparing a substrate for analysis, comprising:
    exposing a first portion of the substrate to an electron beam, wherein a second portion of the substrate not exposed to the electron beam comprises a copper structure;
    exposing the substrate to a fluorine containing chemical, wherein the fluorine containing chemical bonds to the first portion but not the second portion to form a fluorine containing layer on the first portion; and
    exposing the substrate to an etch chemistry, wherein the etch chemistry does not etch the first portion of the substrate due to the fluorine containing layer, and wherein the etch chemistry etches the copper structure in the second portion of the substrate.

18. The method of claim 17, wherein the etch chemistry comprises a chlorine-based chemistry.

19. The method of claim 17, wherein the fluorine containing chemical comprises carbon tetrafluoride.

20. The method of claim 17, wherein the first portion of the substrate comprises an additional copper structure.

21. The method of claim 17, wherein the first portion of the substrate comprises an additional portion of the copper structure.

22. A method for preparing a substrate for analysis, comprising:
    exposing the substrate to a fluorine containing chemical, wherein the fluorine containing chemical bonds to the substrate to form a fluorine containing layer on the substrate; and
    removing the fluorine containing layer and, copper in a first portion of the substrate by directing an electron beam to the first portion in the presence of an etch chemistry, wherein other portions of the substrate not exposed to the electron beam are not removed due to the fluorine containing layer.

23. The method of claim 22, further comprising prior to said exposing, cleaning the substrate to remove oxide present on the substrate.

24. The method of claim 22, further comprising prior to said exposing, directing the electron beam to the substrate to prepare the substrate for bonding with the fluorine containing chemical.

25. The method of claim 22, further comprising during said exposing, directing the electron beam to the substrate, wherein the fluorine containing chemical is substantially inert with respect to the substrate except in the presence of the electron beam.

26. The method of claim 22, wherein the etch chemistry comprises a chlorine-based chemistry.

27. A method for preparing a substrate for analysis, comprising:

removing a portion of a copper structure on the substrate using an etch chemistry in combination with an electron beam, wherein the etch chemistry is substantially inert with respect to the copper structure except in the presence of the electron beam; and inhibiting removal of other portions of the copper structure and other copper structures on the substrate during said removing by exposing the substrate to a fluorine containing chemical during said removing, wherein the fluorine containing chemical will bond with the other portions of the copper structure and the other copper structures on the substrate.

28. The method of claim 27, wherein the etch chemistry comprises a chlorine-based chemistry.

29. The method of claim 27, wherein the fluorine containing chemical comprises xenon difluoride.

* * * * *